US011965018B2

(12) United States Patent
Bergmann et al.

(10) Patent No.: US 11,965,018 B2
(45) Date of Patent: Apr. 23, 2024

(54) CHROMATOGRAPHY SYSTEM AND METHOD FOR CAPTURING A BIOPOLYMER

(71) Applicant: CMC Biologics A/S, Soborg (DK)

(72) Inventors: Simon Bergmann, Hellerup (DK); Mads Laustsen, Gentofte (DK)

(73) Assignee: CMC BIOLOGICS A/S, Soborg (DK)

(*) Notice: Subject to any disclaimer, the term of this patent is extended or adjusted under 35 U.S.C. 154(b) by 141 days.

(21) Appl. No.: 17/588,276

(22) Filed: Jan. 29, 2022

(65) Prior Publication Data

US 2022/0153814 A1 May 19, 2022

Related U.S. Application Data

(63) Continuation of application No. 15/117,019, filed as application No. PCT/EP2015/051801 on Jan. 29, 2015, now Pat. No. 11,267,869.

(30) Foreign Application Priority Data

Feb. 7, 2014 (EP) .................................... 14154324
Mar. 27, 2014 (EP) .................................... 14161900

(51) Int. Cl.
*C07K 16/00* (2006.01)
*B01D 15/18* (2006.01)
(Continued)

(52) U.S. Cl.
CPC .......... *C07K 16/00* (2013.01); *B01D 15/1864* (2013.01); *B01D 15/1885* (2013.01);
(Continued)

(58) Field of Classification Search
CPC ............ B01D 15/1864; B01D 15/1885; B01D 15/20; B01D 15/3804; B01D 15/424;
(Continued)

(56) References Cited

U.S. PATENT DOCUMENTS 6,362,642 B1   3/2002  Farnworth
7,947,813 B2   5/2011  Fahner
(Continued)

FOREIGN PATENT DOCUMENTS

EP   2014760   1/2009
EP   2451963   4/2014
(Continued)

OTHER PUBLICATIONS

U.S. Appl. No. 15/117,059, Notice of Allowance, dated Nov. 15, 2021.
(Continued)

*Primary Examiner* — Latosha Hines
(74) *Attorney, Agent, or Firm* — Cheryl H. Agris; Agris & von Natzmer, LLP

(57) ABSTRACT

The present invention relates to a chromatography system wherein the chromatography system comprises an eluting system and a capturing system consisting of at least two chromatography units operated alone or in series and a capturing process employing in-line buffer dilution in, which concentrated buffers are blended with water and provided to the chromatography units.

26 Claims, 3 Drawing Sheets

(51) Int. Cl.
  *B01D 15/20* (2006.01)
  *B01D 15/38* (2006.01)
  *B01D 15/42* (2006.01)
  *C07K 1/36* (2006.01)
  *C12M 1/26* (2006.01)
  *G01N 30/46* (2006.01)
  *G01N 30/88* (2006.01)

(52) U.S. Cl.
  CPC ......... *B01D 15/20* (2013.01); *B01D 15/3804* (2013.01); *B01D 15/424* (2013.01); *C07K 1/36* (2013.01); *C12M 33/00* (2013.01); *G01N 30/468* (2013.01); *G01N 30/88* (2013.01); *C07K 2317/55* (2013.01); *C07K 2317/622* (2013.01); *G01N 2030/8831* (2013.01)

(58) Field of Classification Search
  CPC ...... C07K 16/00; C07K 1/36; C07K 2317/55; C07K 2317/622; C12M 33/00; G01N 2030/8831; G01N 30/468; G01N 30/88
  See application file for complete search history.

(56) References Cited

U.S. PATENT DOCUMENTS

| | | |
|---|---|---|
| 8,271,139 B2 | 9/2012 | Bellafiore |
| 8,679,778 B2 | 3/2014 | Laustsen |
| 2008/0279038 A1 | 11/2008 | Bellafiore |
| 2011/0073548 A1* | 3/2011 | Williams ........... B01D 15/1871 210/102 |
| 2012/0156783 A1 | 6/2012 | Kubiak |
| 2013/0112624 A1 | 5/2013 | Gebauer |
| 2013/0280788 A1 | 10/2013 | Skudas |
| 2013/0323841 A1 | 12/2013 | Kruglick |
| 2015/0118753 A1 | 4/2015 | Brau |
| 2015/0232505 A1 | 8/2015 | Konstantinov |

FOREIGN PATENT DOCUMENTS

| | | | | |
|---|---|---|---|---|
| WO | 2008153472 | 12/2008 | | |
| WO | WO2008153472 | 12/2008 | | |
| WO | 2010056584 | 5/2010 | | |
| WO | WO2010056584 | 5/2010 | | |
| WO | 2011003153 | 1/2011 | | |
| WO | WO 2011003153 | 1/2011 | | |
| WO | 2012074481 | 6/2012 | | |
| WO | WO2012074481 | 6/2012 | | |
| WO | WO-2012074481 A1 * | 6/2012 | ............ B01D 15/18 |
| WO | 2015075070 | 5/2015 | | |
| WO | WO2015075070 | 5/2015 | | |
| WO | 2015117883 | 8/2015 | | |
| WO | 2015117884 | 8/2015 | | |
| WO | WO2015117883 | 8/2015 | | |
| WO | WO2015117884 | 8/2015 | | |
| WO | 2015158696 | 10/2015 | | |
| WO | WO2015158696 | 10/2015 | | |

OTHER PUBLICATIONS

U.S. Appl. No. 15/117,019, Notice of Allowance, dated Oct. 27, 2021.
Related EP appln. No. 15702220.3, Response to Communication dated Apr. 20, 2021, submitted Oct. 19, 2021.
U.S. Appl. No. 15/117,059, Interview Summary dated Sep. 13, 2021.
U.S. Appl. No. 15/117,019, Interview Summary dated Sep. 13, 2021.
U.S. Appl. No. 15/117,059, Office Action dated May 12, 2021.
U.S. Appl. No. 15/117,019, Office Action dated Apr. 29, 2021.
Related EP appln. No. 15702220, Communication dated Apr. 20, 2021.
U.S. Appl. No. 15/117,059, Office Action dated Oct. 29, 2020.
U.S. Appl. No. 15/117,019, Office Action, dated Oct. 16, 2020.
U.S. Appl. No. 15/117,059, Office Action dated Feb. 27, 2020, 2.
U.S. Appl. No. 15/117,019, Office Action dated Jan. 10, 2020.
U.S. Appl. No. 15/117,019, Interview Summary, dated Dec. 13, 2019.
U.S. Appl. No. 15/117,059, Interview Summary dated Dec. 13, 2019.
U.S. Appl. No. 15/117,059, Office Action dated Jun. 24, 2019.
U.S. Appl. No. 15/117,019, Office Action dated Jun. 13, 2019.
U.S. Appl. No. 15/117,019, Office Action dated Sep. 7, 2018.
U.S. Appl. No. 15/117,059, Restriction Requirement dated Jun. 25, 2018.
Related EP appln. No EP15704231.8, amended claims dated Jun. 22, 2017.
Related EP appln. No. EP15702220.3, response to written opinion, dated Mar. 30, 2017.
Related PCT Appln. No. PCT/EP2015/051801(published as WO2015/117884), International Preliminary Report on Patentability (IPRP), dated Aug. 9, 2016.
Related PCT Appln. No. PCT/EP2015/051797 (published as WO2015/117883), International Preliminary Report on Patentability (IPRP), dated Aug. 9, 2016.
Related PCT Appln. No. PCT/EP2015/051801 (published as WO2015/117884), International Search Report, dated Apr. 28, 2015.
Related PCT Appln. No. PCT/EP2015/051797 (published as WO2015/117883), International Search Report, dated, dated Apr. 28, 2015.
Process Analytical Equipment for Monitoring, Control and Cost Optimization of Inline Dilution Processes turning science into solutions, Jan. 1, 2012 (Jan. 1, 2012), XP055118436, Retrieved from the Internet: URL:http://www_sartorius.de/fileadmin/fm-dam/sartorius_media/Bioprocess-Solutions/Process_Analytical_Technology/Application_Notes/_Appl_PAT_Equipment_for_Inline_Dilution_Processes_W--1125-e.pdf.
U.S. Appl. No. 15/117,059, Office Action dated Sep. 13, 2018.*

* cited by examiner

CHROMATOGRAPHY SYSTEM AND METHOD FOR CAPTURING A BIOPOLYMER

FIELD

The present invention relates to a chromatography system and a method for producing a biopolymer from a medium into an elution buffer using the chromatography system. The methods of the present invention are suitable for use in a manufacturing process for producing a polypeptide such as monoclonal antibodies, in particular for preparing an active pharmaceutical ingredient for a pharmaceutical product.

BACKGROUND

During the last years an increasing focus has be put into the development of new biological medicines and vaccines. Examples of biological medicines include but are not limited to insulin, growth factors, monoclonal antibodies, vaccines, coagulation factors and blood and blood products and the demand for biological medicines, particularly antibodies, has increased markedly. In response to the increased market demands efficient cell culture expression systems have been developed and allowed current biomanufacturing facilities to produce larger product quantities.

As a result of those increasing product quantities, the "bottleneck" in biopharmaceutical production has shifted from upstream production processes toward downstream purification processes. For example, a typical process for downstream processing of monoclonal antibodies involves an affinity purification step (i.e. a capturing step) using a Protein A affinity medium. After the protein A purification step the antibodies are typically further purified by a virus inactivation step followed by other chromatography steps, e.g., bind-elute cation exchange chromatography and/or by bind-elute or flow-through multimodal, mixed mode or anion exchange chromatography and a final nanofiltration purification step.

In such a typical downstream purification process it is commonly the chromatographic capturing step that is presenting significant challenges in terms of facility throughput since, due to the high cost of producing polypeptides including complex monoclonal antibodies the affinity resin is often only saturated until 50-65% of its actual binding capacity during the capturing step to avoid pass through of costly product. In addition the affinity resin in it self is normally also a costly compound. Thus, there is a strong incentive to optimize the utilization of the capturing resin.

For that reason, multicolumn chromatography processes (also called continuous chromatography) has become an object of growing interest. In continuous chromatography, several columns are connected in an arrangement that allows columns to be operated in series and/or in parallel, depending on the method requirements. Thus, all columns can be run in principle simultaneously, but slightly shifted in method steps. The procedure can be repeated, so that each column is loaded, eluted, and regenerated several times in the process. Continuous chromatography (e.g. simulated moving bed (SMB) chromatography) operation may results in a better utilization of chromatography resin, reduced processing time and reduced buffer requirements, all of which benefits process economy. However, SMB chromatography is still not suitable for large scale or cGMP biopharmaceutical production, mainly because it is a complicated method to set up and run, involving the control of a large number of valves and columns.

WO2012074481 discloses a more simple two-column continuous or semi-continuous large-scale chromatographic set up comprising two packed bed chromatography columns, tanks for holding feed, purification buffers, eluate as well as pumps and detectors for controlling the operation of the system where each column is loaded, eluted, and regenerated several times in the process.

Another issue of increasing polypeptide batch sizes is that the amount of purification buffers also increase such that massive amounts of purification buffers have to be prepared daily for large-scale production facilities. Consequently, the capacity of associated buffer preparation systems, buffer hold tanks, and intermediate product hold tanks also increases.

Since, handling and storage of such huge amounts of purification buffers are laborious and expensive and since the affinity resin often only is inadequately used there is an acute need for more efficient industrial large-scale chromatography capturing systems.

The present invention addresses the need for improved and more efficient utilization of chromatography affinity columns and purification buffer handling during capturing of biopolymers, in particular for capturing of complex monoclonal antibodies.

SUMMARY OF THE INVENTION

The present invention provides a chromatography system and a method for producing a biopolymer, from a medium containing the biopolymer and waste products, into an elution buffer. The method employs continuous capturing of the biopolymer onto one or more chromatography units comprising a material having affinity for the biopolymer and, washing and eluting the biopolymer using an eluting system employing inline buffer dilution in which concentrated buffers are blended with water and provided to the chromatography units for separating the biopolymer into an elution buffer and optionally reusing the chromatography units. This system provides several advantages, one advantage being that wash, elution, cleaning and/or equilibration buffers can be mixed from concentrated solutions with water or buffer by inline buffer dilution immediately prior to use, thereby significantly reducing the container size requirements and making the overall process more efficient. Another advantage by employing two or more chromatography units operated alone or in series, is that they can either both be loaded at the same time or each of them can interchangeable be loaded, eluted, and regenerated several times during the purification process. This allows for much more efficient use of the chromatography units in that the biopolymer that is present in a flow-through from the first chromatography unit is captured on the second chromatography unit which allows for complete saturation of the chromatography unit with biopolymer before the biopolymer is washed and eluted from the chromatography unit. Using two chromatography units creates the most simple system which have the advantages mentioned herein, although 3 and 4 chromatography units can be employed this results in a much more complex system to control and also demands more space.

This is illustrated in working example 1 that is directed to chromatography experiments performed in normal mode and in overloaded mode for assessing dynamic binding capacity of protein A chromatography and the quality of the purification step in relation to residual host cell protein and DNA. Overload and normal load chromatography runs were conducted using an agarose based gel (MabSelect SuRe) and a silica based resin (ProVance) resulting in similar yields and purity (see Table 6). However, running the MabSelect SuRe column in overload mode resulted in a product recovery of 65 to 85% higher than running in normal mode. A chromatography run using ProVance in overload mode resulted in an increase in product load capacity of 23%.

Moreover, in a chromatography run where both the load and the column were placed in a thermo cabinet at 35° C. resulted in a 50% reduction in residual DNA contamination and in a 24% reduction in host cell protein. Further advantages will be apparent from the disclosure below.

One aspect of the invention relates to a chromatography system (20) for producing a biopolymer wherein the chromatography system comprises an eluting system (10) and a capturing system (11), wherein the capturing system (11) comprises a feed container (1) for holding a medium comprising the biopolymer and waste products, wherein the feed container (1) has an outlet (16), a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15), wherein the outlet (16) of the feed container (1) is in fluid connection with the inlet (12) of the first chromatography unit (2) and in fluid connection with the inlet (14) of the second chromatography unit (3), wherein a first valve means (31) is located between the outlet (16) and the inlet (12), and a second valve means (32) is located between the outlet (16) and the inlet (14), wherein the outlet (13) of the first chromatography unit (2) is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) is in fluid connection with the inlet (12) of the first chromatography unit (2), and a fourth valve means (34) is located between the outlet (15) of the second chromatography unit (3) and the inlet (12) of the first chromatography unit (2);

wherein the eluting system (10) comprises,
a wash buffer container (4), having an outlet (21),
an elution buffer container (5), having an outlet (22),
optionally a cleaning buffer container (6), having an outlet (23)
optionally an equilibration buffer container (7), having an outlet (24),
a water supply (8), having an outlet (25),
an inline buffer dilution system (9) having an inlet (26a) and an outlet (27), wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9), wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9),
optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9), optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9), wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3).

Another aspect of the invention relates to a method for producing a biopolymer using a chromatography system (20) according to the first aspect, the method comprising:

(a) leading a medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2) until a first pre-determined level of binding capacity is reached in the chromatography unit (2), wherein the fluid connection from the outlet (16) of the feed container (1) to the inlet (14) of the second chromatography unit (3) is closed by the second valve means (32) and wherein the fluid connection from the outlet (13) of the first chromatography unit (2) to the inlet (14) of the second chromatography unit (3) is closed by the third valve means (33), (b) when the first pre-determined level of binding capacity is reached, leading the medium comprising the biopolymer and waste products through the fluid connection from the outlet (13) of the first chromatography unit (2) to the inlet (14) of the second chromatography unit (3) and through the second chromatography unit (3) for a specified setting for the biopolymer un-captured by the first chromatography unit (2) to be captured on the second chromatography unit (3), and medium and waste products continues through the outlet (15) of the chromatography unit (3), until a second pre-determined level of binding capacity is reached in the chromatography unit (2) and/or (3), wherein the fluid connection from the outlet (16) of the feed container (1) to the inlet (14) of the second chromatography unit (3) is closed by the second valve means (32), (c) when the second pre-determined level of binding capacity is reached, leading the medium comprising the biopolymer and waste products through the fluid connection from the outlet (16) of the feed container (1) to the inlet (14) of the chromatography unit (3) wherein the biopolymer is captured on the chromatography unit (3), and medium and waste products continues through the outlet (15) of the chromatography unit (3), until a third pre-determined level of binding capacity is reached in the chromatography unit (2) and/or (3), wherein the fluid connection from the outlet (16) of the feed container (1) to the inlet (12) of the first chromatography unit (2) is closed by the first valve means (31), and wherein the fluid connection from the outlet (15)

of the second chromatography unit (3) to the inlet (12) of the first chromatography unit (2) is closed by the fourth valve means (34), wherein during or after step c)

(i) washing the first chromatography unit (2) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (12) of the first chromatography unit (2), through the first chromatography unit (2), and through the outlet (13) of the first chromatography unit (2), until a first pre-determined level of washing is reached, wherein the fluid connection from the outlet (27) of the inline buffer dilution system (9) to the inlet (14) of the second chromatography unit (3) is closed by the eleventh valve means (41), (ii) when the first pre-determined level of washing is reached, eluting the biopolymer from the chromatography unit (2) by leading:

(a1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(a2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the working solution ready elution buffer the outlet (27) of the inline buffer dilution system (9) to the inlet (12) of the first chromatography unit (2), through the first chromatography unit (2), and through the outlet (13) of the first chromatography unit (2), until a first pre-determined level of eluating is reached, and collecting the eluate, wherein the fluid connection from the outlet (27) of the inline buffer dilution system (9) to the inlet (14) of the second chromatography unit (3) is closed by the eleventh valve means (41), (d) when the third pre-determined level of binding capacity is reached, leading the medium through the fluid connection from the outlet (15) of the second chromatography unit (3) to the inlet (12) of the first chromatography unit (2) and through the first chromatography unit (2) for a specified setting for the biopolymer un-captured by the second chromatography unit (3) to be captured on the first chromatography unit (2), and medium and waste products continues through the outlet (13) of the chromatography unit (2) until a fourth pre-determined level of binding capacity is reached in the chromatography unit (2) and/or (3), wherein the fluid connection from the outlet (16) of the feed container (1) to the inlet (12) of the first chromatography unit (2) is closed by the first valve means (31), (e) when the fourth pre-determined level of binding capacity is reached, leading the medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2), until a fifth pre-determined level of binding capacity is reached in the chromatography unit (2) and/or (3), wherein the fluid connection from the outlet (16) of the feed container (1) to the inlet (14) of the second chromatography unit (3) is closed by the second valve means (32), wherein during or after step e)

(iii) washing the chromatography unit (3) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (14) of the second chromatography unit (3), through the second chromatography unit (3), and through the outlet (15) of the second chromatography unit (3), until a second pre-determined level of washing is reached, wherein the fluid connection from the outlet (27) of the inline buffer dilution system (9) to the inlet (12) of the first chromatography unit (2) is closed by the tenth valve means (40), (iv) when the second pre-determined level of washing is reached, eluting the biopolymer from the second chromatography unit (3) by leading:

(b1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(b2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the diluted elution buffer through the outlet (27) of the inline buffer dilution system (9) to the inlet (14) of the second chromatography unit (3), through the second chromatography unit (3), and through the outlet (15) of the second chromatography unit (3), until a second pre-determined level of eluating is reached, and collecting the eluate, wherein the fluid connection from the outlet (27) of the inline buffer dilution system (9) to the inlet (12) of the first chromatography unit (2) is closed by the tenth valve means (40), (f) optionally, repeating step (a) to (e), and (g) optionally, purifying the biopolymer from the collected eluate(s).

In a further aspect, the invention relates to the use of a chromatography system as described herein for producing a biopolymer from a medium comprising the biopolymer and waste products.

Further objects of the present invention will become apparent in view of the present description, figures, examples and claims.

DEFINITIONS

Figure 1:
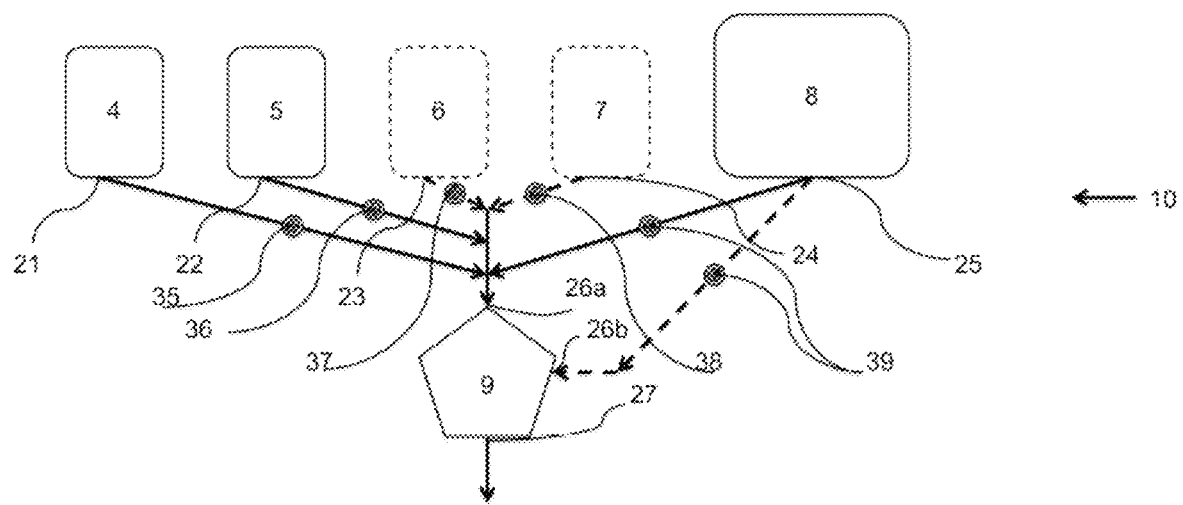
FIG. 1 is a schematic illustration of an eluting system employing an inline buffer dilution system.

Prior to a discussion of the detailed embodiments of the invention is provided a definition of specific terms related to the main aspects and embodiments of the invention.

Chromatography System

As used herein the term "chromatography system" refers to any device or system for capturing a biopolymer from a medium comprising the biopolymer and waste products. Integral parts of a chromatography system includes chromatographic units allowing for capturing the biopolymer from a medium comprising the biopolymer and waste products and means for washing and eluting the biopolymer and/or the waste products from the capturing device.

Biopolymer

As used herein the term "biopolymer" means a polypeptide, protein, nucleic acid or virus particle, which can be native or biologically or synthetically modified, including fragments, multimers, aggregates, conjugates, fusion products etc. Examples of polypeptides of interest that may be produced using the systems and methods of the invention include recombinant therapeutic proteins such as antibodies or fragments thereof, blood clotting factors, cytokines, enzymes, peptide hormones, etc. Specific examples of such proteins include human growth hormone, follicle-stimulating hormone, Factor VIII, Factor VII, Factor IX, erythropoietin (EPO), granulocyte colony-stimulating factor (G-CSF), alpha-galactosidase A, alpha-L-iduronidase (rhIDU; laronidase), N-acetylgalactosamine-4-sulfatase (rhASB; galsulfase), DNAse, tissue plasminogen activator (TPA), glucocerebrosidase, interferons (IF) such as interferon-alpha, interferon-beta and interferon-gamma, insulin, insulin derivatives, insulin-like growth factor 1 (IGF-1), tenecteplase, antihemophilic factor, human coagulation factor, and etanercept; and antibodies such as Trastuzumab, Infliximab, Basiliximab, Belimumab, Daclizumab, Adalimumab, Abciximab, Afutuzumab, Alemtuzumab, Cetuximab, Daclizumab, Denosumab, Eculizumab, Edrecolomab, Golimumab, Ibritumomab tiuxetan, Mepolizumab, Motavizumab, Natalizumab, Ofatumumab, Omalizumab, Oregovomab, Palivizumab, Pemtumomab, Pertuzumab, Ranibizumab, Rituximab, Tefibazumab and Zanolimumab.

Capturing System

As used herein the term "capturing system" refers to a part of the chromatography system that contains a feed container holding a medium, two or more chromatography units that allows for capturing the biopolymer, optionally one or more waste container(s) and one or more eluate container(s) for collecting the biopolymer.

The term "feed container" as used herein refers to any kind of container, e.g. a rigid tank of e.g. steel, glass or plastic or a collapsible and/or disposable bag, that holds a medium.

As used herein the term "medium" refers to a liquid comprising a biopolymer and waste products that is provided to a chromatography system for separating the biopolymer from the waste products. The biopolymer can be a polypeptide, such as a monoclonal antibody. Examples of a medium can be a clarified fermentation broth, a biological fluid etc. as well as a liquid originating from a previous separation step and comprising a partially purified biopolymer.

As used herein the term "waste and waste products" refers to chemical or biological compounds produced by cells present in a bioreactor or which arise from cells that die or break open during a fermentation process. Impurities can also derive from a growth medium or from a previous separation process. Impurities may comprise ethyl alcohol, butyl alcohol, lactic acid, acetone ethanol, gaseous compounds, peptides, lipids, ammonia, aromatic compounds and DNA and RNA fragments or brake down products of the biopolymer.

As used herein the term "chromatography unit" refers to a separate chromatography device, such as a column or a filter unit that may hold any kind of material having higher affinity for the biopolymer than the waste products thereby allowing for its separation.

As used herein the term "affinity" refers to the selective adsorption of the biopolymer onto an affinity ligand. The affinity ligand can bind to a defined site on the biopolymer and may be attached to an inert chromatographic support. The affinity ligand can also interact with the biopolymer through ionic interactions. When the medium containing the biopolymer passes through the chromatographic support, the biopolymer binds to the solid support via interaction of the binding site, or through ionic interactions, with the immobilized ligand. The specifically bound biopolymer can then be recovered by changing the environmental conditions (pH, ionic strength, solvents) to weaken the binding interaction.

Eluting System

The term "eluting system" as used herein refers to a part of the chromatography system that contains one or more wash buffer container(s) holding concentrated wash buffer, one or more elution buffer containers holding concentrated or working solution ready elution buffer, a water/buffer supply and an inline buffer dilution system that is in fluid connection with the wash buffer(s), the elution buffer(s) and the water/buffer supply. Optionally the eluting system also comprises one or more cleaning buffer container(s) and equilibration buffer container(s).

The term "working solution ready elution buffer" refers to an elution buffer where no dilution or adjustment is required.

The term "wash buffer container", "elution buffer container", "cleaning buffer container" and "equilibration buffer container" as used herein refers to any kind of container, e.g. a rigid tank of e.g. steel, glass or plastic or a collapsible and/or disposable bag, that holds a wash buffer, an elution buffer, a cleaning buffer and an equilibration buffer, respectively.

The term "inline buffer dilution system" refers to a system of mixing a concentrated solution and water (or some other diluent, e.g. an aqueous buffer) inside a processing line to produce a normal strength, process-ready solution. Inline dilution systems (sometimes called "on-site blending systems") also provide many advantages over purchasing pre-mixed and diluted buffers. The inline buffer dilution system may, in its most simple form, be a system consisting of tubes or pipes from which concentrated wash, elution, cleaning and equilibration buffer and water/buffer, respectively, are supplied, and that connect with each other at one end before being led into the inlet of the chromatography units. It may also be a static mixer or a dynamic mixer. There exist several types of static mixers such as so called plate-type mixers or mixers wherein the mixing elements are contained in a cylindrical (tube) or squared housing. In the plate type design mixing is accomplished through intense turbulence in the flow. The housed-elements mixer's fixed can simultaneously produce patterns of flow division and radial mixing. However, more typically the inline buffer dilution system will be a more advanced automated system that allows two or more liquid streams to be brought together in a controlled fashion to meet a target diluted solution concentration. Inline dilution systems are commercially available from different suppliers such as from Novasep, GE Healthcare or for example the system IBD™ 1K Inline Buffer Dilution System from Asahi Kasei Bioprocess (disclosed in U.S. Pat. No. 8,271,139). Such systems are capable of making multi-component blends of up to 20× concentrates and produce a ready-to-use solution offering total blend flow rates of more than 1000 L/h.

As used herein, the term "water supply" is intended to encompass any supply of water, such as a tank, a container, or a tube, for use in diluting the concentrated wash buffer, elution buffer, cleaning buffer or equilibration buffer. This can include any supply of suitable water, such as pure water, high-purity water (HPW) or water for injection (WFI) whether stored in a tank or other container or supplied as needed in purified form using e.g. ultrafiltration or reverse osmosis. Due to problems measuring the pH of high-purity water, the water from the water supply may be buffered, with for example, an acid, a base or a salt.

As used herein the term "a valve means" is intended to encompass any device by which the flow of fluid through a passageway, such as a connection line, may be blocked, permitted, or otherwise regulated by a movable part that shuts, opens, or partially obstructs, respectively, the fluid flow, including but not limited to 2-, 3- or 4-way valves. A valve means is one valve or is more valves, as may be desired, for instance the valve means (31) between outlet (16) of the container (1) and the inlet (12) of the first chromatography unit (2) may constitute one valve or may be 2, 3, or 4 valves as desired. Valves can be manually, magnetically, electrically, pneumatically or hydraulically operated If using flexible tubing pinch valves are particularly suitable.

The term "fluid" as used herein is intended to define any substance which flows and therefore includes liquids and gases which are able to flow.

As used herein the term "in fluid connection" means that fluid, such as liquid, e.g. medium, can flow between an inlet of one container, tank or unit and an outlet of another container, tank or unit. The fluid connection may be interrupted by one or more valves and/or holding containers such that the flow of fluid through the fluid connection can be started and stopped whenever decided. Typically, most of the parts of the chromatography system that are in fluid connection have a fluid connection that may be interrupted. For example, if a buffer container is in fluid connection with a chromatography unit this means that a flow of the buffer to the chromatography unit can be realized if decided, but typically there is at least one valve located in the fluid connection between the buffer container and the chromatography unit, such that the fluid flow can be stopped when decided and started when decided.

As used herein the term "inlet" is intended to encompass any means that enables the introduction of fluid into a container, tank or unit, and is an opening which is typically equipped with a fitting whereto for instance a tube or a valve can be connected. An inlet of a chromatography unit is for example the end-fitting of a chromatography column to which the fluid connection(s) can be attached.

As used herein the term "outlet" is intended to encompass any means that enables the fluid to leave a container, tank or unit and is an opening which is typically equipped with a fitting whereto for instance a tube or a valve can be connected. An outlet of a chromatography unit is for example the end-fitting of a chromatography column to which the fluid connection(s) can be attached.

As used herein the term "means for leading the fluid" is intended to encompass any means that can convey a fluid, e.g. a liquid, comprising a biopolymer and waste products or a buffer from a container or the inline buffer dilution system through a pipe, tube or connection line to for example a chromatography unit, a waste container, an elution buffer container or to the inline buffer dilution system. Such means could be mediated by gravity or hydraulic force, but typically, it will be a pump. As used herein the term "a pump" is intended to encompass any pumping device suitable for conveying a fluid, e.g. a liquid. Typically, it may either be a separate pumping device or an individual channel in a multichannel pumping device, such as e.g. a multichannel peristaltic pump. Examples of pumps include membrane pumps, hose pumps/peristaltic pumps, valve-less pumps and diaphragm pumps.

As used herein the term "pre-determined level of binding capacity" refers generally to a desired level of binding capacity of the chromatography unit. The binding capacity of an affinity ligand may be determined empirically and is for example dependent on the loading conditions e.g. flow rate and the temperature.

As used herein the term "binding capacity" refers to the amount of biopolymer that the ligand (e.g., beads packed in a column) can bind under equilibrium conditions if every available binding site on the beads is utilized.

As used herein the term "specified setting" is intended to encompass any specified time period necessary for the biopolymer that is un-captured by the first chromatography unit to be captured on the second chromatography unit. It is also intended to encompass any specified amount of medium or biopolymer that passes un-captured by the first chromatography unit to be captured on the second chromatography unit.

DETAILED DESCRIPTION OF THE INVENTION

Figure 2:
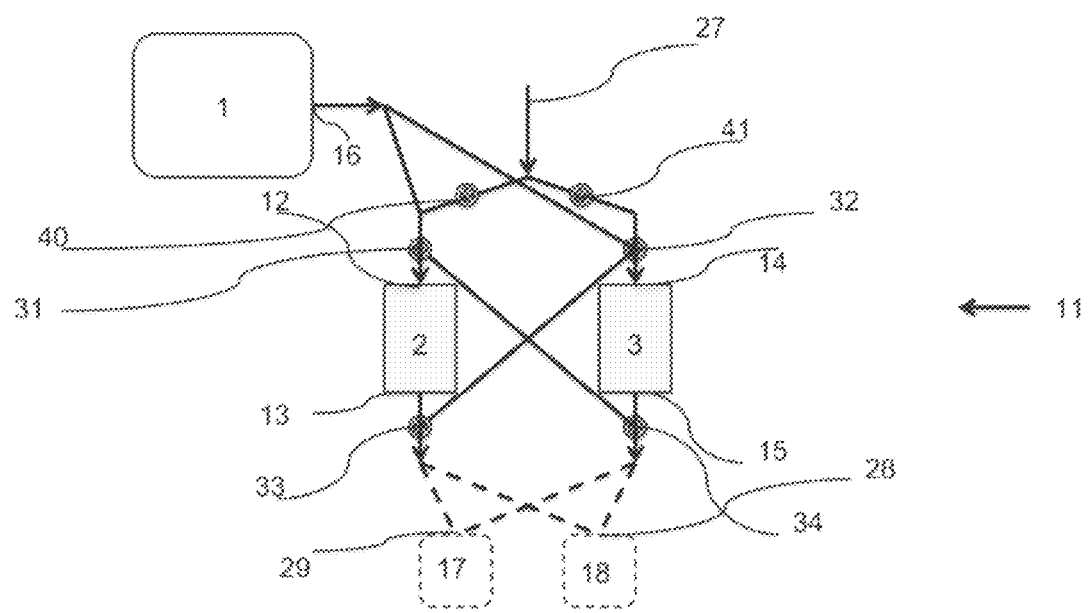
FIG. 2 is a schematic illustration of a two column capturing system.
Figure 3:
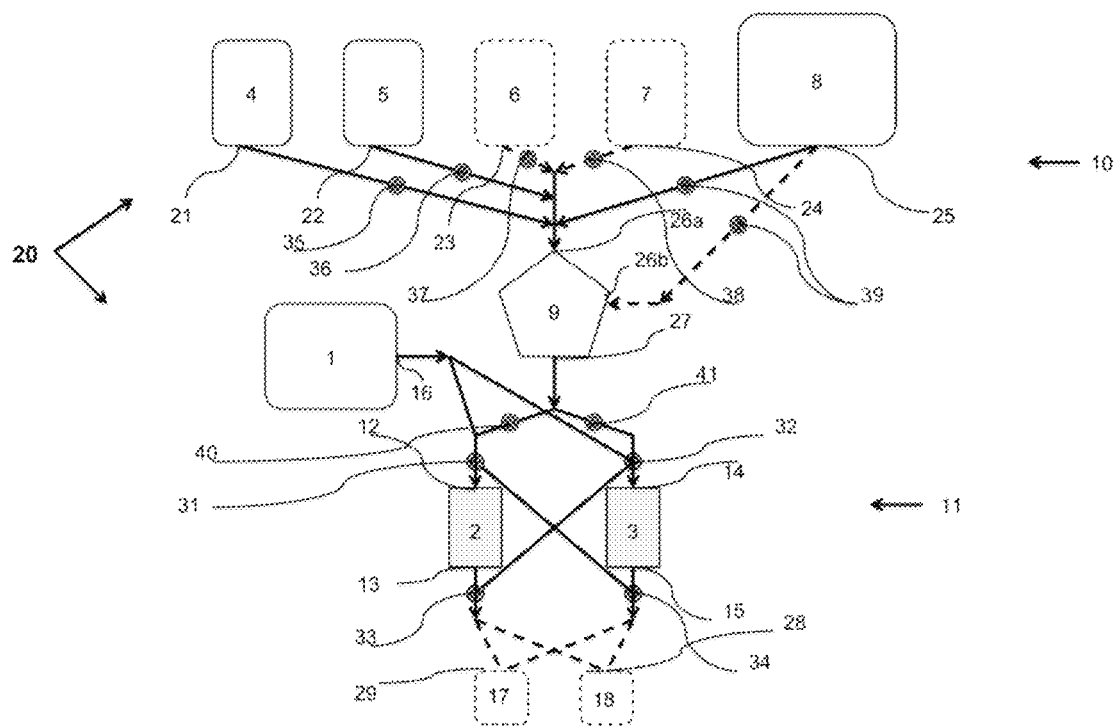
FIG. 3 is a schematic illustration of a complete chromatography system.

The chromatography system (20) of the present invention illustrated, without any limitation, in FIGS. 1-3 and includes an eluting system (10) and a capturing system (11). The capturing system (11) comprises a feed container (1) for holding a medium comprising the biopolymer and waste products, wherein the feed container (1) has an outlet (16), a first chromatography unit (2) and a second chromatography unit (3) both comprising material having affinity for the biopolymer. The first chromatography unit (2) has an inlet (12) and an outlet (13) and the second chromatography unit (3) has an inlet (14) and an outlet (15). The outlet (16) of the feed container (1) is in fluid connection with the inlet (12) of the first chromatography unit (2) and also in fluid connection with the inlet (14) of the second chromatography unit (3). A first valve means (31) is located between the outlet (16) and the inlet (12), and a second valve means (32) is located between the outlet (16) and the inlet (14). The outlet (13) of the first chromatography unit (2) is in fluid connection with the inlet (14) of the second chromatography unit (3), and a third valve means (33) is located between the outlet (13) of the first chromatography unit (2) and the inlet (14) of the second chromatography unit (3). The outlet (15) of the second chromatography unit (3) is in fluid connection with the inlet (12) of the first chromatography unit (2), and a fourth valve means (34) is located between the outlet (15) of the second chromatography unit (3) and the inlet (12) of the first chromatography unit (2).

The eluting system (10) comprises, a wash buffer container (4), having an outlet (21),
an elution buffer container (5), having an outlet (22), optionally a cleaning buffer container (6), having an outlet (23) optionally an equilibration buffer container (7), having an outlet (24), a water supply (8), having an outlet (25) and an inline buffer dilution system (9) having an inlet (26a) and an outlet (27). The outlet (21) of the wash buffer container (4) is in fluid connection with the inlet (26a) of the inline buffer dilution system (9) where a fifth valve means (35) is located. The outlet (22) of the elution buffer container (5) is in fluid connection with the inlet (26a) of the inline buffer dilution system (9) where a sixth valve means (36) is located. The outlet (25) of the water supply (8) is in fluid connection with the inlet (26a) of the inline buffer dilution system (9) or with a separate inlet (26b) of the inline buffer dilution system (9) where a ninth valve means (39) is located. The outlet (27) of the inline buffer dilution system (9) is in fluid connection with the inlet (12) of the first chromatography unit (2) and in fluid connection with the inlet (14) of the second chromatography unit (3). A tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3). The outlet (23) of the optional cleaning buffer container (6) is in fluid connection with the inlet (26a) of the inline buffer dilution system (9) where a seventh valve means (37) is located and also the outlet (24) of the optional equilibration buffer container (7) is in fluid connection with the inlet (26a) of the inline buffer dilution system (9) where an eighth valve means (38) is located.

In one embodiment of the present invention the chromatography system can consist of 3 and 4 or more chromatography units. However, such system is a very complex system to control and also demands more space. Using only two chromatography units creates a simpler system which have the advantages easy operation and handling. In a preferred embodiment of the present invention the chromatography system consist of one first chromatography unit (2) and one second chromatography unit (3).

In an other embodiment of the present invention the biopolymer is a recombinant protein such as an antibody or a fragment thereof, where a fragment can e.g. be a Fab fragment, Fv fragment or single chain Fv (scFv) fragment.

A typical process for downstream processing of monoclonal antibodies involves an affinity purification step (i.e., a capturing step) using a Protein A affinity medium. After the protein A purification step the antibodies are typically further purified by a virus inactivation step followed by other chromatography steps, e.g., bind-elute cation exchange chromatography and/or by bind-elute or flow-through multimodal or anion exchange chromatography and a final nanofiltration purification step. The chromatography system of the present invention may either operate as part of such a purification process or it may operate as an independent unit and contain additional components such as containers for holding waste and eluate.

In one embodiment of the present invention the chromatography system comprises a waste container (17) having an inlet (29) wherein the waste container (17) is in fluid connection with the outlet (13) of the first chromatography unit (2), wherein the third valve means (33) is located between the outlet (13) of the first chromatography unit (2) and the inlet (29) of the waste container (17). In an other embodiment of the present invention the chromatography system comprises a waste container (17) having an inlet (29) wherein the waste container (17) is in fluid connection with the outlet (15) of the second chromatography unit (3), wherein the fourth valve means (34) is located between the outlet (15) of the second chromatography unit (3) and the inlet (29) of the waste container (17). An advantage of this is, that the waste can be saved and re-purified if significant amounts of biopolymer may be present in the waste fraction.

According to the present invention the eluate may be directly provided to additional chromatography and/or filtration systems for further purification in which case no eluate container is necessary. The eluate may also be collected and used as it is, or it may be stored for further purification of the biopolymer. In one embodiment of the present invention the chromatography system comprises an eluate container (18) having an inlet (28) wherein the eluate container (18) is in fluid connection with the outlet (13) of the first chromatography unit (2), wherein the third valve means (33) is located between the outlet (13) of the first chromatography unit (2) and the inlet (28) of the elution buffer container (18). In another embodiment of the present invention the chromatography system comprises an eluate container (18) having an inlet (28) wherein the eluate container (18) is in fluid connection with the outlet (15) of the second chromatography unit (3), wherein the fourth valve means (34) is located between the outlet (15) of the second chromatography unit (3) and the inlet (28) of the eluate container (18).

Further additional components of the chromatography system are pumps for leading the medium and/or buffers through the system, degassers, debubblers and/or bubble traps devices as well as detectors for monitoring the operation of the system, including the flow of medium and/or buffers.

Pumps may either be a separate pumping device or an individual channel in a multichannel pumping device, such as e.g. a multichannel peristaltic pump. Peristaltic pumps are convenient to use in disposable bioprocessing systems as they do not add any fluid-contact surfaces and they are well adapted for leading of fluids in parallel in that one pump head can be used with several tubes. It is possible to use only one multichannel pump for the entire chromatography system, but it is also possible to use several multichannel pumps. If different flow rates are to be used in different connection lines, it is possible to use tubing of different diameters in the channels of a multichannel peristaltic pump. Further, it is possible to stop the flow in a separate line by releasing the compression of the tubing on the rollers of the pump.

Pumps can be connected to the outlets of the feed container (1), wash buffer (4), elution buffer (5), cleaning buffer (6) or equilibration buffer container (7) or to the outlet of the water supply (8). Pumps can also be connected to inlets or outlets of the inline buffer dilution system (9) or to inlets or outlets of the first chromatography unit (2) or the second chromatography unit (3). The skilled person knows how to elect and place suitable pumps for leading the medium and buffers to the chromatography units.

In one embodiment of the present invention the chromatography system comprises a means for leading the medium comprising biopolymer and waste, such as a pump. In an other embodiment of the present invention the chromatography system further comprise a means for leading the wash buffer, a means for leading the elution buffer, a means for leading the cleaning buffer, a means for leading the equilibration buffer, a means for leading the water, and a means for leading the diluted buffer, such as a pump. In a further embodiment of the present invention a pump is located between the outlets (21), (22), (23), (24) and (25) and the inlet (26a) and/or (26b) of the inline buffer dilution system. In a still further embodiment of the present invention a pump is located between the outlet (16) of the feed container (1) and the inlets (12) and/or (14) of the chromatography unites (2) and (3).

During complex operation of liquids, bubbles may form and affect the flow of the liquid through the connection lines and/or through the chromatography units. Bubbles caught in the chromatography units may be especially problematic for maintaining correct flow through the system. Thus, degassers, debubblers and/or bubble traps devices may for example be located before or after the inline buffer dilution system or before the chromatography unit (2) and/or (3). The skilled person knows how to elect the most suitable degassers, debubblers and/or bubble traps devices and where to locate them in the chromatography system.

In one embodiment of the present invention the chromatography system comprises a bubble trap located before the inlet (12) of the first chromatography unit (2) and/or a bubble trap located before the inlet (14) of the second chromatography unit (3). In another embodiment of the present invention the chromatography system comprises a bubble trap located before the inlet (26a) or (26b) of the inline buffer dilution system.

Detectors suitable for monitoring the concentration of the biopolymer or the waste products can be connected to the outlets of the first chromatography unit (2) and/or the second chromatography unit (3). Typical, detectors include single or multi-wavelength UV monitors, refractive index detectors, light scattering detectors flow detectors, mass detectors and near-infrared (NIR) sensors. The skilled person knows how to elect the most suitable detector depending on the affinity material in the chromatography units and the biopolymer.

Detectors suitable for monitoring the flow rates or pressure to and from the inline buffer dilution system can be connected to the inlets (26a) and (26b) and/or to the outlet (27) of the inline buffer dilution system (9). Detector(s) for monitoring the blend quality from the inline dilution e.g. pH conductivity of the blended solutions can be connected to the outlet (27) of the inline buffer dilution system (9).

In one embodiment of the present invention the chromatography system comprises a detector suitable for monitoring the concentration of a biopolymer and/or for measuring conductivity or pH of the blended solution.

In an other embodiment of the present invention the chromatography system comprises a detector suitable for monitoring the concentration of the biopolymer such as single or multi-wavelength UV monitors, refractive index detectors, light scattering detectors flow detectors, mass detectors and near-infrared (NIR) sensors. A programmable logic controller may integrate the operation and control of all components in the system.

According to the present invention the chromatography units are separate chromatography devices, such as columns or filter units that may hold any kind of material having higher affinity for the biopolymer than the waste products thereby allowing for its separation. The ligand that binds to a defined site on the target biopolymer may be attached to an inert chromatographic support. The ligand can also interact with the biopolymer through ionic interactions. When the medium containing the biopolymer passes through the chromatographic support, the biopolymer binds to the solid support via interaction of the binding site, or through ionic interactions, with the immobilized ligand. The specifically bound biopolymer can then be recovered by changing the environmental conditions (pH, ionic strength, solvents) to weaken the binding interaction.

One advantage of this type of chromatography is the reduced number of steps required for attaining the desired biopolymer purity. The chromatography unit may be a chromatography column adapted to be packed with a particulate chromatography resin such as a packed bed chromatography column. It can be an axial or radial column and may comprise a column tube, an inlet porous bed support and an outlet porous bed support, an inlet fluid distributor and an outlet fluid distributor. When packed with the chromatography resin, the resin bed can fill essentially the entire volume between the inlet and outlet porous bed supports. Packed bed chromatography columns may be packed with a resin having affinity towards the biopolymer such as a proteinaceous ligand. The proteinaceous ligand may be derived from Protein A, Protein G, Protein L or an antibody. It can be either a native or recombinant protein A, G, L or antibody or it can be a mutant, fragment or multimer of any of these proteins such as alkali-tolerant recombinant protein A ligand, such as a MABSELECT SURE® or a ProVance® ligand. Such ligands can have very high selectivity and are hence suited for capture of valuable biopharmaceuticals from complex feeds.

In a further embodiment of the present invention the material having affinity for the biopolymer is a rigid, high-flow matrix and alkali-tolerant recombinant protein A ligand, such as a MABSELECT SURE® or a ProVance® ligand.

In some embodiments the chromatography unit may also be based on microporous membrane absorbers as stationary support having the affinity ligands coupled to an activated membrane a hydrogel such as NATRIX®. In general, there are three types of membrane modules used for protein separation: flat sheet, hollow fiber and radial flow. Preferred membrane materials for bioseparations are cellulose, polyamide, polyethylene and polyethersulfone. For membrane chromatography there are some commercially available membranes containing reactive groups, ready for ligand attachment. Sartobind Epoxy®, conceived by Sartorius (Germany), is a regenerated cellulose membrane with nominal pore size of 0.45 μm possessing epoxy groups for the coupling of ligands containing —OH, —NH2 or —SH groups. Another example is Ultrabind® US450 (Pall Corp., USA), which is a polysulfone membrane with 0.45 μm pore size containing aldehyde groups.

The inline buffer dilution system may have inline monitoring and control of the dilution process using instrumentation such as mass flow meters and/or analytical instruments such as pH, conductivity or near-infrared (NIR)

instrumentation. A programmable logic controller may integrate the operation and control of the inline buffer dilution system.

There are several approaches for operating the blend procedure in the inline buffer dilution system. For example, some systems blend the final solution based on conductivity and/or pH data provided by conductivity and pH process analyzers, whereas other systems use volumetric flow rate as the primary means of control, since inline pH and conductivity meters have an inherent tendency to drift and improper calibration may result in false readings.

The inline buffer dilution system may employ two or more concentrated wash, elution, cleaning and/or equilibration buffer containers, e.g. containing different buffer components. In this case, the system may be constructed such that different buffer components having different concentrations are led into a single mixing chamber by different inlets at different flow rates and diluted in the mixing chamber with water or buffer to the desired concentration, whereafter the diluted mixture is provided to the chromatography units. Another option, in the case of multiple buffer containers, is for each buffer container to be connected to a separate mixing chamber for dilution with water or buffer. The separate mixing chambers can be further connected to a common mixing chamber, wherein diluted buffer from two or more individual separate mixing chambers is mixed together before being led into the chromatography units via a single inlet, or alternatively, diluted buffer from individual separate mixing chambers may be conveyed to the chromatography units by way of multiple inlets, e.g. one inlet for each mixing chamber.

In one embodiment of the present invention the inline buffer dilution system has a total blend flow rate of at least 1 L/min, such as at least 2 L/min, such as at least 5 L/min, such as at least 10 L/min.

The use of two or more buffer containers may be advantageous in order to be able to further reduce container size, space requirements, etc., for example by using one container to hold one buffer component and another container to hold another buffer component. Another possibility is to have a first wash buffer comprising certain components in a concentrated form in one wash buffer container and a second wash buffer comprising other components in a concentrated form in a second wash buffer container.

Similarly, it may be advantageous to have two or more cleaning and/or equilibration buffer containers holding different cleaning compounds in different concentration for efficient cleaning and/or equilibration of the chromatography units.

Since the elution buffer, in some cases, has to be prepared within very exact specification ranges for pH, conductivity and/or osmolality, the elution buffer may either be present in the container in a more concentrated form than the concentration that is provided to the chromatography units or it may be present in the container in the same concentration as the concentration that is provided to the chromatography units for eluting the biopolymer (i.e. as a working solution ready). In situations where the elution buffer is present in the container as a working solution ready buffer the outlet (22) of the elution buffer container (5) may be in direct fluid connection with the inlet (12) of the first chromatography unit (2) and/or with the inlet (14) of the second chromatography unit (3). In other words the outlet (22) of the elution buffer container (5) is directly connected with the inlet (12) of the first chromatography unit (2) and/or with the inlet (14) of the second chromatography unit (3). Another possibility is that the outlet (22) of the elution buffer container (5) is in fluid connection with the inline buffer dilution system (9) is in fluid connection with the inlet (12) of the first chromatography unit (2) and/or with the inlet (14) of the second chromatography unit (3) through an independent inlet and outlet of the of the inline buffer dilution system.

In one embodiment of the present invention the outlet (22) of the elution buffer container (5) is in direct fluid connection with the inlet (12) of the first chromatography unit (2) and/or with the inlet (14) of the second chromatography unit (3).

In another embodiment of the invention, the eluting system may comprise two or more wash, eluting, cleaning and equilibration buffer containers, each of which is in fluid communication with an inlet of the inline buffer dilution system.

In further embodiment of the present invention at least one of the wash, elution, cleaning or equilibration buffer containers has a volume of at least 10 L, such as at least 50 L, such as at least 100 L, e.g. at least 250 L.

The elution buffer may also be prepared as a gradient from the concentrates by the inline buffer dilution system. Such a gradient may either simply be prepared from two stock solutions having for example different salt concentrations or pH's or it can be prepared form multi-component concentrates having for example both different metal ion concentrations, salt concentrations and pH's.

If desired, a holding step can be used following mixing of the concentrated wash, elution, cleaning and equilibration buffer(s) with the water to produce the respective diluted buffers. The eluting system of the invention may therefore optionally include a "holding container", e.g. a holding tank, between the inline buffer dilution system and the chromatography units, i.e. such that the outlet of the inline buffer dilution system is in indirect fluid connection with the chromatography units. The holding tank/container may function not only to temporarily hold the diluted buffer, but may also, if desired, be adapted to provide additional mixing of the diluted buffer before it is provided to the chromatography units. This may e.g. be advantageous when using multiple buffer containers.

During operation of the present chromatography system, medium comprising the biopolymer is provided to the chromatography units and the biopolymer is captured by the affinity ligand e.g. resin whereby binding sites for the absorbing biopolymer get occupied and the binding capacity decreases. The pre-determined levels of binding capacity may independently be set such that the resin for example is loaded to about 30%400%, including greater than about 30%, greater than about 40%, greater than about 50%, greater than about 60%, greater than about 70%, greater than about 80%, greater than about 90%, and greater than about 98%, of its binding capacity. The pre-determined levels of binding capacity may also be set independently such that only 0.5% at the most, 1% at the most, 2% at the most, 5% at the most, 10% at the most, 15% at the most or 20% at the most of the biopolymer in the medium passes through the outlet (13) or (15) of the chromatography units (2) or (3) to a waste or holding container. Typically, the first, second, third, fourth and fifth pre-determined level of binding capacity will be determined independently, and adjusted such that the pre-determined level of binding capacity is reached after a specific time period of loading. Such a time period may be set from about 15 minutes to about 24 hours, such as from about 30 minutes to about 24 hours, such as from about 1 hour to about 24 hours, such as from about 2 hours to about 24 hours, such as from about 4 hours to about 24 hours, such as from about 6 hours to about 24 hours, such as from about 8 hours to about 24 hours, such as from about 10 hours to about 24 hours, such as from about 12 hours to about 24 hours, such as from about 1 hour to about 20 hours, such as from about 2 hours to about 18 hours, such as from about 2 hours to about 16 hours, such as from about 2 hours to about 12 hours, such as from about 2 hours to about 10 hours, such as from about 2 hours to about 8 hours, such as from about 2 hours to about 6 hours.

However, the first pre-determined level of binding capacity will typically be set such that it allows sufficient time for washing, eluting and optionally cleaning and equilibrating the chromatography unit (2) such that chromatography unit (3) can be connected to the chromatography unit (3), before the chromatography unit (2) becomes saturated or overloaded with biopolymer and the biopolymer escapes from being captured onto the chromatography unit (2). In one embodiment of the present invention the first pre-determined level of binding capacity is set to avoid biopolymer in the medium through the outlet (13) of the first chromatography unit (2) and/or the outlet (15) of the second chromatography unit (3). In a further embodiment the first pre-determined level of binding capacity is set so that the resin is loaded to about 30%-100% of its binding capacity. In a still further embodiment the first pre-determined level of binding capacity is set so that 20% at the most of the biopolymer in the medium passes through the outlet (13) of the chromatography unit (2) to a waste or holding container.

The second pre-determined level of binding capacity of step (b) may typically be set such that the chromatography unit (2) becomes fully saturated with biopolymer, while allowing sufficient binding capacity of the chromatography unit (3) such that the chromatography unit (2) can be washed, eluted, cleaned and equilibrated before biopolymer begin to escape from being captured on the chromatography unit (3). In one embodiment of the present invention the second pre-determined level of binding capacity is set to avoid biopolymer in the medium through the outlet (13) of the first chromatography unit (2) and/or through the outlet (15) of the second chromatography unit (3). In a further embodiment the second pre-determined level of binding capacity is set so that the resin is loaded to about 30%-100% of its binding capacity. In a still further embodiment the second pre-determined level of binding capacity is set so that 20% at the most of the biopolymer in the medium passes through the outlet (15) of the second chromatography unit (3) to a waste or holding container.

The third pre-determined level of binding capacity of step (c) may typically be set such that it allows sufficient time for washing, eluting and optionally cleaning and equilibrating the chromatography unit (2) such that chromatography unit (2) can be connected to the chromatography unit (3), before the chromatography unit (3) becomes saturated or overloaded with biopolymer and the biopolymer escapes from being captured onto the chromatography unit (3). In one embodiment of the present invention the third pre-determined level of binding capacity is set to avoid biopolymer in the medium through the outlet (13) of the first chromatography unit (2) and/or through the outlet (15) of the second chromatography unit (3). In a further embodiment the third pre-determined level of binding capacity is set so that the resin is loaded to about 30%-100% of its binding capacity. In a still further embodiment the third pre-determined level of binding capacity is set so that 20% at the most of the biopolymer in the medium passes through the outlet (15) of the second chromatography unit (3) to a waste or holding container.

The fourth pre-determined level of binding capacity of step (d) may typically be set such that the chromatography unit (3) becomes fully saturated with biopolymer, while allowing sufficient binding capacity of the chromatography unit (2) such that the chromatography unit (3) can be washed, eluted, cleaned and equilibrated before biopolymer begin to escape from being captured on the chromatography unit (2). In one embodiment of the present invention the fourth pre-determined level of binding capacity is set to avoid biopolymer in the medium through the outlet (13) of the first chromatography unit (2) and/or through the outlet (15) of the second chromatography unit (3). In a further embodiment the fourth pre-determined level of binding capacity is set so that the resin is loaded to about 30%-100% of its binding capacity. In a still further embodiment the fourth pre-determined level of binding capacity is set so that 20% at the most of the biopolymer in the medium passes through the outlet (13) of the first chromatography unit (2) to a waste or holding container.

The fifth pre-determined level of binding capacity of step (e) may typically be set such that it allows sufficient time for washing, eluting and optionally cleaning and equilibrating the chromatography unit (3) such that chromatography unit (3) can be connected to the chromatography unit (2), before the chromatography unit (2) becomes saturated or overloaded with biopolymer and the biopolymer escapes from being captured onto the chromatography unit (3). In one embodiment of the present invention the fifth pre-determined level of binding capacity is set to avoid biopolymer in the medium through the outlet (13) of the first chromatography unit (2) and/or through the outlet (15) of the second chromatography unit (3). In a further embodiment the fifth pre-determined level of binding capacity is set so that the resin is loaded to about 30%-100% of its binding capacity. In a still further embodiment the fifth pre-determined level of binding capacity is set so that 20% at the most of the biopolymer in the medium passes through the outlet (13) of the first chromatography unit (2) to a waste or holding container.

An advantage of operating the chromatography units in series according to the present invention is that the chromatography unit first chromatography unit can be loaded until most or all binding sites for absorbing the biopolymer are occupied. When more and more of the binding sites get occupied by the biopolymer there are less and less binding sites available for waste products i.e. impurities. Moreover, since the biopolymer has higher affinity for the affinity ligand e.g. the resin waste products get displaced from the chromatography unit such that a much more pure biopolymer can be produced.

The washing steps may be carried out using a single wash buffer or by using several wash buffers of different composition. The pre-determined levels of washing may be determined by monitoring the amount of waste components that flow through the chromatography unit using suitable detectors such UV detectors of optical density detectors. Often, the pre-determined levels of washing is determined in initial experiments and converted to the amount of wash buffer necessary for the desired pre-determined level of washing to be obtained. Typically, wash buffers are used in volumes of 3 to 20 times the volume of the chromatography unit. The skilled person knows how to select suitable wash buffers depending on the chromatography unit used and the biopolymer to be produced. Typical example of wash buffers are 15-50 mM Na-phosphate with 0.15-0.5 M NaCl at pH 6.5-7.5.

In one embodiment the first pre-determined level of washing is set to avoid biopolymer in the wash buffer through the outlet (13) of the chromatography unit (2). In a further embodiment the second pre-determined level of washing is set to avoid biopolymer in the wash buffer through the outlet (15) of the chromatography unit (3).

The elution steps may be carried out using a single elution buffer, by using several elution buffers of different composition or by using an elution gradient. The pre-determined levels of elution may be determined by monitoring the amount of biopolymer that flow through the chromatography unit using suitable detectors and set to when no biopolymer or nearly no biopolymer is detected. Often, the pre-determined levels of elution is determined in initial experiments and converted to the amount of elution buffer necessary for the desired pre-determined level of washing to be obtained. Typically, elution buffers are used in volumes of 3 to 20 times the volume of the chromatography unit. The skilled person knows how to select suitable elution buffers depending on the chromatography unit used and the biopolymer to be produced. Typical examples of elution buffers include citrate buffers having a pH from about 3 to about 4.

In one embodiment the first pre-determined level of eluating is set to contain biopolymer in the elution buffer through the outlet (13) of the chromatography unit (2). In another embodiment the second pre-determined level of eluating is set to contain biopolymer in the elution buffer through the outlet (15) of the chromatography unit (3).

In an other embodiment the pre-determined levels of eluating is set independently such that less than 50%, less than 25%, less than 15%, less than 10%, less than 8%, less than 5%, less than 2,5%, less than 1%, less than 0,5% of the maximum level detected in the elution buffer is present when the eluating is completed.

The method for producing a biopolymer according to the present invention is based on repeatedly loading, washing and eluting the biopolymer. Consequently, the chromatography units (2) and (3) has to be repeatedly connected and disconnected. However, during the first round of the capturing the biopolymer, the chromatography unit (2) may either be operated alone, i.e. where the fluid connection from the outlet (13) of the first chromatography unit (2) to the inlet (14) of the second chromatography unit (3) is closed by the third valve means (33) or it may be operated as connected with chromatography unit (2), i.e. wherein the fluid connection from the outlet (13) of the first chromatography unit (2) to the inlet (14) of the second chromatography unit (3) is open by the third valve means (33).

In one embodiment of the present invention step (a) can be conducted leading a medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2) until a first pre-determined level of saturated binding capacity is reached in the chromatography unit (2), wherein the fluid connection from the outlet (16) of the feed container (1) to the inlet (14) of the second chromatography unit (3) is closed by the second valve means (32) and wherein the fluid connection from the outlet (13) of the first chromatography unit (2) to the inlet (14) of the second chromatography unit (3) is open by the third valve means (33).

In an other embodiment of the present invention the chromatography system may be arranged using disposable chromatography units, also called single use or chromatography units that are discarded after the biopolymer has been eluted from the chromatography units and replaced new chromatography units after their use. In another embodiment of the present invention the chromatography system is arranged using multi use chromatography units that are repeatedly loaded, eluted, cleaned and regenerated.

Cleaning of the chromatography units may be carried out using a single cleaning buffer or by using several cleaning buffers of different composition.

The pre-determined levels of cleaning may be determined by monitoring the amount of waste products that flow through the chromatography unit using suitable detectors. Often, the pre-determined levels of elution is determined in initial experiments and converted to the amount of cleaning buffer necessary for the desired pre-determined level of cleaning to be obtained. Typically, cleaning buffers are used in volumes of 3 to 20 times the volume of the chromatography unit. The skilled person knows how to select suitable cleaning buffers depending on the chromatography unit used and the biopolymer to be produced. Typical examples of cleaning buffers include 0.1-0.5 M NaOH.

In one embodiment of the present invention after step (ii);
(iia) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of cleaning is reached, wherein the fluid connection from the outlet (27) of the inline buffer dilution system (9) to the inlet (14) of the second chromatography unit (3) is closed by the eleventh valve means (41) and, wherein after step (iv);
(iva) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (14) of the second chromatography unit (2), through the second chromatography unit (3), and through the outlet (15) of the second chromatography unit (3), until a second-determined level of cleaning is reached, wherein the fluid connection from the outlet (27) of the inline buffer dilution system (9) to the inlet (12) of the first chromatography unit (2) is closed by the tenth valve means (40).

During operation of multi use chromatography units for purification of antibodies, such as protein A based columns, waste products tend to accumulate in the upper part of the chromatography units. In such a situation it may be an advantages to provide the cleaning buffer to the outlets (13) and (15) of the chromatography unit (2) and (3) leading it through the chromatography unit (2) and (3) and through the inlets (12) and (14) of the chromatography units, to for example a waste container or holding tank, to facility efficient cleaning of the chromatography units.

In a preferred embodiment of the present invention after step (ii), (iib) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (13) of the first chromatography unit (2), through the first chromatography unit (2), and through the inlet (12) of the first chromatography unit (2), until a first pre-determined level of cleaning is reached, wherein the fluid connection from the outlet (27) of the inline buffer dilution system (9) to the inlet (14) of the second chromatography unit (3) is closed by the tenth valve means (40) and, wherein after step (iv);

(ivb) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (15) of the second chromatography unit (3), through the second chromatography unit (3), and through the inlet (13) of the second chromatography unit (3), until a second-determined level of cleaning is reached, wherein the fluid connection from the outlet (27) of the inline buffer dilution system (9) to the inlet (14) of the first chromatography unit (2) is closed by the eleventh valve means (41).

In a further embodiment of the present invention after step (iia) and (iib), (iic) equilibrating the first chromatography unit (2) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the inlet (12) of the first chromatography unit (2), until a first pre-determined level of equilibration is reached, wherein the fluid connection from the outlet (27) of the inline buffer dilution system (9) to the inlet (14) of the second chromatography unit (3) is closed by the eleventh valve means (41), and wherein after step (iva) or (ivb);

(ivc) equilibrating the second chromatography unit (3) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of equilibration is reached, wherein the fluid connection from the outlet (27) of the inline buffer dilution system (9) to the inlet (14) of the first chromatography unit (2) is closed by the valve means (40).

In a still further embodiment of the present invention the inlet (29) of the waste container (17) is in fluid connection with the outlet (13) of the first chromatography unit (2) and in fluid connection with the outlet (15) of the second chromatography unit (3).

In a further embodiment of the present invention the inlet (28) of the eluate container (18) is in fluid connection with the outlet (13) of the first chromatography unit (2) and in fluid connection with the outlet (15) of the second chromatography unit (3).

In a still further embodiment of the present using a means for leading the medium comprising biopolymer and waste, such as a pump.

In a further embodiment of the present using a detector suitable for monitoring the concentration of the biopolymer such as a UV absorption detector, a refractive index detector or a light scattering detector.

The steps of cleaning (iia), (iva), (iib) and (ivb) the chromatography units (2) and (3) may be followed by steps of equilibrating the chromatography for making them ready for receiving the biopolymer. Typical examples of equilibration buffers include 5-40 mM sodium phosphate with 20-250 mM NaCl at pH 6.5-7.5.

The temperature of the medium and the wash, elution, cleaning and equilibration buffer may have an influence on the stability of the biopolymer and also on the binding of the biopolymer to the chromatography units. The temperature may also have an influence on how impurities such as residual DNA and host cell proteins binds to the protein A ligand. The skilled person knows how to select suitable temperature condition for operating the chromatography system.

In one embodiment the medium in the feed container may be kept at a temperature of e.g. 28-38° C., such as about 32° C. or such as about 35° C. for enhancing the affinity to the first or second chromatography unit or both. In another embodiment the wash, elution, cleaning and/or equilibration buffers are used at a temperature of e.g., 28-38° C., such as about 32° C. or such as about 35° C. In a further embodiment the wash, elution, cleaning and/or equilibration buffers are used at a temperature in the range of 1-10° C. In a still further embodiment the wash, elution, cleaning and/or equilibration buffers are used at a temperature in the range of 10-30° C. In a further embodiment the medium in the feed container has a temperature of e.g. 28-38° C. and the wash, elution, cleaning and/or equilibration buffers are used at a temperature in the range of 1-10° C.

In a still further embodiment the chromatography system (20) is kept at a temperature of e.g. 28-38° C., such as about 32° C. or such as about 35° C.

In a further embodiment of the present invention the capturing system (11) is kept at a temperature of e.g. 28-38° C., such as about 32° C. or such as about 35° C. for enhancing removal of residual DNA and/or host cell protein.

During normal operating conditions the feed container may be repeatedly filled up and steps (a) to (e) are repeated until the all the desired medium has been provided to the chromatography system and all the corresponding biopolymer has been produced. In case the produced biopolymer is not sufficiently pure it may be subjected to further down stream purification and filtration procedures for removal of residual impurities. For removal of residual impurities such as host cell proteins, host cell DNA, protein A residues, viruses and/or aggregated antibodies, the biopolymer may be further purified by a virus inactivation step followed by other chromatography steps, e.g. bind-elute cation exchange chromatography and/or by bind-elute or flow-through multimodal or anion exchange chromatography and a final nanofiltration purification step.

DETAILED DRAWING DESCRIPTION

The following non-limiting drawing descriptions are for example purposes only.

The chromatography system (20) of the invention in its most simple form comprises an eluting system and a capturing system. For simplicity the eluting system (10) is illustrated in FIG. 1, the capturing system (11) in FIG. 2 and the complete chromatography system (20) in FIG. 3.

The eluting system (10) illustrated in FIG. 1 shows a wash buffer container (4) having an outlet (21), an elution buffer container (5) having an outlet (22), a water supply (8) having an outlet (25) and with dashed lines a cleaning buffer container (6) having an outlet (23) and an equilibration buffer container (7) having an outlet (24), all of which are in fluid connection with an inline buffer dilution system (9) having an inlet (26a) and an outlet (27), through connection lines connecting the outlets (21, 22, 23, 24, 25) to the inlet (26a) of the inline buffer dilution system. Each of the outlets (21, 22, 23, 24, 25) or the corresponding fluid connection(s) also have at least one valve means (35, 36, 37, 38, 39) for regulating the flow from each of the containers to the inline buffer dilution system. The dashed lines representing the cleaning buffer container (6), the equilibration buffer container (7) and the corresponding fluid connection indicates that these components are optional features of the system. Moreover, the fluid connection connecting the outlet (25) of the water supply (8) to the inlet (26a) of the inline buffer dilution system may either be using the same inlet as the connection lines connecting the outlets (21, 22, 23, 23 24) with inlet (26a) or alternatively, as shown with a dashed line, be using a separate inlet (26b).

The capturing system (11) illustrated in FIG. 2 shows a feed container (1) having an outlet (16), a first chromatography unit (2) having an inlet (12) and an outlet (13), a second chromatography unit (3) having an inlet (14) and an outlet (15) and, optionally represented by dashed lines, a waste container (17) having and an inlet (29) and an eluate container (18) having an inlet (28). Also is shown the outlet 27 of the inline buffer dilution system (9). The outlet 16 of the feed container (1) is in fluid connection both with the inlet (12) of the chromatography unit (2) and the inlet (14) of the chromatography unit (3) through the fluid connection connecting the outlet (16) with the inlets (12) and (14). Each of the inlets (12) and (14), the outlet (16) or the fluid connection have at least one valve means (31, 32). In addition, the inlet (12) of the chromatography unit (2) is in fluid connection with the outlet (15) of chromatography unit (3), and the inlet (14) of the chromatography unit (3) is in fluid connection with the outlet (13) of chromatography unit (2) through connection lines connecting outlet (13) with inlet (14) and outlet (15) with inlet (12), and each of the outlets (13) and (15) or the corresponding fluid connections have at least one valve means (33, 34). The outlet (13) of the chromatography (2) is also in liquid connection with the inlet (29) of the waste container (17) and the inlet (28) of the eluate container (18) through fluid connection connecting the outlet (13) with the inlet (29) and the inlet (28) with outlet (13) (showed with dashed lines). The outlet (27) of the inline dilution buffer system (9) is in fluid connection with the inlet (12) of chromatography unit (2) and the inlet (14) of the chromatography unit (3) through fluid connection connecting outlet (27) with the inlets (12) and (14) each of the fluid connection having valve means (40) and (41). The outlet (27) is also in fluid connection with the outlet (13) of chromatography unit (2) and the outlet (15) of the chromatography unit (3).

The chromatography system (20) illustrated in FIG. 3 shows the eluting system (10) of FIG. 1 and the capturing system (11) of FIG. 2 connected through the outlet 27 of the inline buffer dilution system (9).

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless other-wise indicated herein or otherwise clearly contradicted by context.

The terms "a" and "an" and "the" and similar referents as used in the context of de-scribing the invention are to be construed to cover both the singular and the plural, unless otherwise indicated herein or clearly contradicted by context. Thus, "a" and "an" and "the" may mean at least one, or one or more.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

EXAMPLES

Example 1 is directed to experiments regarding dynamic binding capacity of protein A chromatography and assessing the quality of the purification step in relation to residual host cell protein and DNA. Example 2 is directed in-line dilution of concentrated buffers.

| Abbreviations and Definitions | |
|---|---|
| Abbreviation | Text |
| ANP | Analytical Procedure |
| CIP | Clean in Place |
| $DBC_{10\%}$ | Dynamic Binding Capacity at 10% breakthrough |
| DPD | Downstream Process Development |
| HCP | Host Cell Protein |
| HMW | High Molecular Weight |
| LEP | Laboratory Experimental Protocol |
| LMW | Low Molecular Weight |
| N/A | Not applicable |
| PA-HPLC | Protein A HPLC |
| PR | Protocol |
| Res. DNA | Residual DNA |
| RT | Room Temperature |

TABLE 4

Buffers used for the studies

| No. | Name | Item no. | | Used for |
|---|---|---|---|---|
| Buffer A | 16% Ethanol 16.7% of 96% Ethanol | HPW 96% ethanol | 1-0003 C0866 | Storage of chromatography systems and column Packing of columns |
| Buffer B | 0.1M Sodium Hydroxide 0.399% Sodium Hydroxide | HPW NaOH | 1-0003 1-0080 | Column CIP pH adjustment of buffers |
| Buffer C | 0.1M Sodium Chloride 0.583% Sodium Chloride | HPW NaCl | 1-0003 1-0026 | HETP equilibration |
| Buffer D | 0.5M Sodium Chloride 2.87% Sodium Chloride | HPW NaCl | 1-0003 1-0026 | HETP test |
| Buffer E | 20 mM sodium phosphate, 150 mM NaCl, pH 7.0 ± 0.2 0.205% di-sodium hydrogen phosphate•2H$_2$O 0.132% sodium di-hydrogen phosphate•2H$_2$O 0.877% sodium chloride | HPW Di-sodium hydrogen phosphate•2H$_2$O Sodium di-hydrogen phosphate•2H$_2$O NaCl | 1-0003 1-0047 1-0266 1-0026 | Equilibration, wash, end elution, wash after elution |
| Buffer F | 20 mM citrate, 100 mM NaCl, pH 3.4 ± 0.2 0.138% tri-sodium citrate•2H2O 0.294% citric acid, anhydrous 0.585% sodium chloride | HPW Tri-sodium citrate•2H2O Citric acid, anhydrous NaCl | 1-0003 1-0187 1-0416 1-0026 | Elution |

TABLE 4-continued

Buffers used for the studies

| Buffer G | 20 mM citrate, 100 mM NaCl, pH 6.0 ± 0.2 0.514% tri-sodium citrate•2H2O 0.049% citric acid, anhydrous 0.585% sodium chloride | HPW Tri-sodium citrate•2H2O Citric acid, anhydrous NaCl | 1-0003 1-0187 1-0416 1-0026 | Dilution of eluate |
| Buffer H | 1.0M Bis Tris, pH 10.0 11.8% Bis Tris | HPW Bis Tris | 1-0003 1-0519 | pH adjustment |
| Buffer I | 1M Sodium Hydroxide (technical quality) 12.5% of 32% Sodium Hydroxide | HPW NaOH | 1-0003 C3567-COA | CIP of Äkta-system, buffer pH adjustment |
| Buffer J | 1% Nitric acid 1.45% of 69% Nitric acid | HPW HNO₃ | 1-0003 1-0108 | CIP of Äkta-system |
| Buffer K | 0.1M Phosphoric Acid, 0.98% Phosphoric Acid of 85% | HPW H₃PO₄ | 1-0003 1-0063 | Column CIP, ProVance |

| No. | Name | Item no. | Dilution Factor | Used for |
|---|---|---|---|---|
| Buffer B10 | 1M Sodium Hydroxide 3.99% Sodium Hydroxide | HPW NaOH | 10 | Column CIP pH adjustment of buffers |
| Buffer E10 | 200 mM sodium phosphate, 1.5M NaCl, pH 7.0 ± 0.2 1.51% di-sodium hydrogen phosphate•2H₂O 1.80% sodium di-hydrogen phosphate•2H₂O 8.77% sodium chloride | HPW Di-sodium hydrogen phosphate•2H₂O Sodium di-hydrogen phosphate•2H₂O NaCl | 10 | Equilibration, wash, end elution, wash after elution |
| Buffer F10 | 200 mM citrate, 1.0M NaCl pH 3.4 ± 0.2 1.38% tri-sodium citrate•2H2O 2.94% citric acid, anhydrous 5.85% sodium chloride | HPW Tri-sodium citrate•2H2O Citric acid, anhydrous NaCl | 10 | Elution |
| Buffer B-Dil | 0.1M Sodium Hydroxide 10% Buffer B10 90% HPW | Buffer B10 HPW | 1:10 | Column CIP pH adjustment of buffers |
| Buffer E-Dil | 20 mM sodium phosphate, 150 mM NaCl, pH 7.0 ± 0.2 10% Buffer E10 90% HPW | Buffer E10 HPW | 1:10 | Equilibration, wash, end elution, wash after elution |
| Buffer F-Dil | 20 mM citrate, 100 mM NaCl pH 3.4 ± 0.2 10% Buffer F10 90% HPW | Buffer F10 HPW | 1:10 | Elution |

Example 1

The purpose of this experiment was to purify material from bioreactors using a Protein A Chromatography column at normal and overloaded conditions. The Quantitative and qualitative output was evaluated for the two setups at room temperature and at 35° C. simulating capturing of product directly from the bioreactor.

Two different Protein A resins were tested:
MabSelect SuRe from GE Health Care based on an Agarose gel. Column CIP performed by 0.1 M Sodium Hydroxide.
ProVance from Grace based on a Silica matrix mainly for single campaign-use chromatography. Column CIP performed by 0.1 M Phosphoric Acid.

As the Protein A Chromatography step is the first step of normally three steps with separation power, any remaining impurity (aggregate, HCP and res. DNA) will be reduced by the subsequent process steps.

Process Description

The overall scope was to establish a continuously chromatographic setup combining two columns according to the present invention used for overload chromatography e.g. combined with a bioreactor using continuously harvesting by perfusion technology.

The tests described in this protocol examined the performance of a column by the conditions described in Table 1 below.

| Experiment | Resin | Loading | Temperature | LEP no. # |
|---|---|---|---|---|
| 1 | MabSelect SuRe from GE | Overloading with 20-40% break through Set point: 49 mg/mL | Room temperature | LEP.2802 |
| 2 | | Overloading with 20-40% break through Set point: 49 mg/mL | 35° C. | LEP.2621 |
| 3 | | Normal load at 70-80% of maximum DBC Set point: 28 mg/mL | Room temperature | LEP.2622 |
| 4 | | Overloading with 20-40% break through Set point: 60 mg/mL | Room temperature | LEP.2919 |
| 5 | | Overloading with 20-40% break through Set point: 60 mg/mL | 35° C. | LEP.2920 |
| 6 | ProVance from Grace | Overloading with 20-40% break through Set point: 68 mg/mL | Room temperature | LEP.2803 |
| 7 | | Normal load at 70-80% of maximum DBC Set point: 39 mg/mL | Room temperature | LEP.2804 |

Equipment

The Protein A Chromatography runs were performed using Åkta Explorer, pH meter, Conductivity meter, Nano-Drop for determination of protein concentration by OD280 and balances Methods Test of Protein A Chromatography The parameter settings for the Protein A Chromatography CIP-cycles and chromatography runs are shown in the tables below.

| Parameter settings | | |
|---|---|---|
| Parameter description | Parameter set points | Unit |
| Default linear flow-CIP | 200[1] | cm/h |
| Flow direction | Downflow | N/A |

[1]Flow for ProVance was adjusted to 100 cm/h to maintain a constant contact time

| MabSelect SuRe CIP procedure before run | | | |
|---|---|---|---|
| CIP procedure | Phase name | Inlet | Outlet |
| 3 CV of buffer B[1] (downflow) | CIP | B1 | F1 |
| No Pause | — | — | — |
| 5 CV of buffer E (upflow) | Equilibration | A11 | F1 |

[1]Buffer K used for CIP of ProVance

| Parameter setting for | | |
|---|---|---|
| Parameter description | Parameter set points | Unit |
| Column flow direction-equilibration and run | Upflow | N/A |
| Column flow direction-Sanitization | Downflow | N/A |
| Default linear flow-equilibration and wash | (5.8 mL/min) 350[1] | cm/h |
| Default linear flow-load and elution | (3.3 mL/min) 200[2] | cm/h |
| Target of Load | See table 1 | mg/mL resin |

[1]Flow for ProVance was adjusted to 175 cm/h to maintain a constant contact time
[2]Flow for ProVance was adjusted to 100 cm/h to maintain a constant contact time

| MabSelect SuRe chromatographic procedure | | | |
|---|---|---|---|
| Chromatographic procedure | Phase name | Inlet | Outlet |
| 2 CV of buffer E-Autozero after 1.9 CV | Equilibration | A11 | F1 |
| Load product | Load | A15 | [1] |
| 30 CV of buffer E | Wash[2] | A11 | F1[1] |
| 15 CV of buffer F Collection: Start ≥ 100 mAU. End ≤ 100 mAU | Elution | A13 | F2 |
| 5 CV of buffer E | Equilibration | A11 | F1 |

[1]load and the two first CV's of wash is collected in suitable fractions to enable determination of the Dynamic Binding Capacity
[2]2 CV at 200 cm/h followed by 28 CV at 350 cm/h Test of Protein A Chromatography The sampling setup for the Protein A Chromatography runs are shown in Table 5 below.

TABLE 5

| Analytical procedure: | pH | Conductivity | Conc. By OD280 | PA-HPLC | SE-UPLC |
|---|---|---|---|---|---|
| ANP no | DPD | DPD | DPD | CMC00853 | CMC08266 |
| Sample Volume (mL) | | | | | 1 |
| Storage condition | +5 °C. | | | | |
| Load sample | x | x | | x | |
| Flow through | | | | x | |
| Protein A Chromatography after neutralization and filtration | x | x | x | x | x |

| Analytical procedure: | Res. DNA[1] | HCP | Res. ProA | SDS PAGE (Red) | SDS PAGE (Non-Red) |
|---|---|---|---|---|---|
| ANP no | CMC02095 | CMC00747 | CMC05331 | CMC00048 | CMC00329 |
| Sample Volume (mL) | 2 | 1 | 1 | 1 | 1 |
| Storage condition | | | −80 °C. | | |
| Load sample | | | | x | x |
| Flow through | | | | | |
| Protein A Chromatography after neutralization and filtration | 2x | x | x | x | x |

Test of MabSelect SuRe Protein A Chromatography.

Chromatographic profiles for Protein A Chromatography with MabSelect SuRe at overload and normal load were obtained (not shown).

The chromatographic profiles (not shown) of the MabSelect SuRe runs performed as expected with the following comments:

Length of load peak for the overload runs was as expected longer than the load peak for the normal load.

Length of wash fraction was increased to 30 CV to ensure sufficient washout of unbound material. The length of the wash will be reduced in further experiments to the length needed to achieve the required reduction of unbound material.

The volume and height of the elution peak were;
36.7 mL and 3.15 AU for the normal load run (LEP2622),
40.4 mL and 3.20 AU for the overload run (LEP2802) and
39.1 mL and 3.29 AU for the overload run (LEP2621) including storage of load at 35° C.
39.7 mL and 2.9 AU for the overload run (LEP2919).
39.7 mL and 2.9 AU for the overload run (LEP2920) loaded at 35° C.

(Peak height was not visualizing the actual peak height as the AU-values are above the max. of the UV-monitor).

No significant difference in yield and purity was observed by loading at room temperature or 35° C., which simulates loading harvest from perfusion directly to the column.

The Dynamic Binding Capacity at 10% (DBC10%) breakthrough was approx. 48 mg/mL resin.

Test of ProVance Protein a Chromatography.

Chromatographic profiles for Protein A Chromatography with ProVance at overload and normal load were obtained (not shown).

The chromatographic profiles of for the ProVance runs were similar to MabSelect SuRe runs and performed as expected with the following comments:

Length of wash fraction was increased to 30 CV to ensure sufficient washout of unbound process liquid. The length of the wash will be reduced to the length needed to achieve the required reduction of unbound material.

The volume and height of the elution peak was;
9.4 mL and 2.96 AU for the normal load run (LEP2804),
13.6 mL and 3.05 AU for the overload run (LEP2803).

Peak height is not visualizing the actual peak height as the AU-values are above the max. of the UV-monitor.

The Dynamic Binding Capacity at 10% (DBC10%) breakthrough is approx. 41 mg/mL resin.

Analytical data generated for quantitative and qualitative evaluation of the Protein A Chromatography runs are listed in Table 6. The data are commented below for each type of resin:

MabSelect SuRe:
  Maximum amount of product loaded on MabSelect SuRe during overload runs was 45 to 49 mg/mL resin, which vary due to variation on the PA-HPLC assay. DBC10% was 48 mg/mL resin for MabSelect SuRe.
  Yields for these runs were between 85 and 107%; in average 95% and depended on the variation on quantification of the load by PA-HPLC and eluate by OD280.
  Product recovery for the normal load run was 25.8 mg/mL resin resulting in a yield at 101%.
  The Size Exclusion profile of the eluates from the normal and overload runs were similar.
  The pattern for product and impurities detected by reduced SDS PAGE and non-reduced SDS PAGE, were similar.
  The process related impurities; relative HCP, residual DNA and residual Protein A are all at the same level.
  No major difference in yield and purity by loading at room temperature or 35° C. However, a major reduction in residual DNA contamination in host cell protein when loading at 35° C. was observed.

ProVance:
  Product recovery on ProVance during overload runs was 38 mg/mL resin, which was approx. 20% lower than the capacity of MabSelect SuRe. DBC10% is 41 mg/mL resin for ProVance.
  Yields for overload—as well as normal-run were 95%, which was at a similar level compare to runs with MabSelect SuRe.
  The Size Exclusion profile (monomer/HMW/LMW) of the eluates is 94.0/3.6/2.4% for the normal run and 92.6/4.8/2.5% for the over load run.
  The pattern for product and impurities detected by reduced SDS PAGE and non-reduced SDS PAGE, show similarity (see Appendix 1 and Appendix 2)
  The process related impurities; relative HCP, residual DNA and residual Protein A are all at the same level.

TABLE 6

Analytical data generated for quantitative and qualitative evaluation of Protein A Chromatography.

| Analytical procedure: ANP no Type of resin | Ref. | Mode | Load ratio mg/mL resin | Pro-duct reco-very mg/mL resin | Temp ° C. | Yield % | Conc. By OD280 DPD mg/mL | PA-HPLC CMC00853 mg/mL | SE-UPLC, Purity CMC08266 % |
|---|---|---|---|---|---|---|---|---|---|
| MabSelect SuRe | LEP2621 | Overload | 44.9 | 47.9 | 35[2] | 107% | 6.2 | 6.7 | 93.7 |
| MabSelect SuRe | LEP2622 | Normal load | 25.8 | 26.0 | RT | 101% | 3.7 | 3.7 | 94.1 |
| MabSelect SuRe | LEP2802 | Overload | 49.1 | 43.5 | RT | 89% | 6.1 | 6.6 | 93.8 |
| MabSelect SuRe | LEP2919 | Overload | 49.4 | 45.0 | RT | 91% | 6.4 | 6.9 | 94.8 |
| MabSelect SuRe | LEP2920 | Overload | 52.7[5] | 44.7 | 35[3] | 85% | 5.6 | 5.9 | 94.2 |
| ProVance | LEP2803 | Overload | 39.8 | 38.3 | RT | 96% | 5.0 | 5.0 | 92.6 |
| ProVance | LEP2804 | Normal load | 32.8 | 31.1 | RT | 95% | 4.6 | 4.5 | 94.0 |

TABLE 6-continued

| Analytical procedure: ANP no Type of resin | SE-UPLC, HMW CMC08266 % | SE-UPLC, LMW CMC08266 % | Res. DNA CMC02095 pg/mL | Relative Res. DNA CMC02095 pg/mL | HCP CMC00747 ng/mL | Relative HCP CMC00747 ng/mL | Res. ProA CMC05331 ng/mL | Relative Res. ProA CMC05331 ng/mL |
|---|---|---|---|---|---|---|---|---|
| MabSelect SuRe | 4.2 | 2.1 | 2538.0 | 378.8 | 193.0 | 28.8 | <20 | <4.2 |
| MabSelect SuRe | 3.8 | 2.1 | 1492.0 | 403.2 | 156.0 | 42.2 | <10 | <2.7 |
| MabSelect SuRe | 4.1 | 2.1 | N/A | N/A | 195.0 | 29.5 | <10 | <1.5 |
| MabSelect SuRe | 3.5 | 1.7 | N/A | N/A | 228 | 33.0 | <130 | <18.8 |
| MabSelect SuRe | 4.1 | 1.7 | N/A | N/A | 118 | 20.0 | <130 | <22.0 |
| ProVance | 4.8 | 2.5 | 1098.0 | 219.6 | 178.0 | 35.6 | <10 | <2.0 |
| ProVance | 3.6 | 2.4 | 2401.0 | 533.6 | 158.0 | 35.1 | <10 | <2.2 |

[1] C: Compare to reference
[2] Load stored at 35 °C., but as column and tubing were stored at room temperature, the temperature of the load has decreased significantly before reaching the column.
[3] Column and load was stored in Thermo Cabinet at 35 C.
[5] Loading was increased to enable higher binding to the resin, which result in lower yield. Flow through calculated based on an average of product concentration of the fractions Conclusion.

Overload and normal load chromatography runs were conducted using an agarose based gel (MabSelect SuRe) and a silica based resin (ProVance) resulting in similar yields and purity (see Table 6).

However, running the MabSelect SuRe (LEP2622) in normal mode, the product recovery was 26.0 mg/mL resin and in overload mode (LEP2621; 47.9 mg/mL resin), (LEP2802; 43.5 mg/mL resin), (LEP2919; 45.0 mg/mL resin) and (LEP2920; 44.7 mg/mL resin), respectively. Accordingly, running the MabSelect SuRe column in overload mode resulted in a product recovery of 65 to 85% higher than running in normal mode.

A chromatography run using ProVance in normal mode (LEP2803) resulted in a product recovery of 31.1 mg/mL resin and in overload mode (LEP2804) of 38.3 mg/mL, which is an increase in product load capacity of 23%.

In addition, the chromatography run (LEP2920) where both the load and the column were placed in a thermo cabinet at 35° C. resulted in a 50% reduction in residual DNA contamination (735 pg/mL compared to 1492 pg/mL) and a 24% reduction in host cell protein 118 ng/mL compared to 156 ng/mL.

Example 2

The purpose of this example was to establish a setup with in-line dilution of concentrated buffers, in this case with 10 times concentration of the original buffer according to the present invention.

The tests described in this example will examine the preparation of the concentrated buffers and comparison after dilution with the original buffer described in Table 2.

TABLE 2

Test setup for preparing of concentrated buffers.

| Activity | Description |
|---|---|
| 1 | Prepare each original buffers three times for MabSelect SuRe chromatography (see Table 4) in order to establish a good reference for pH and conductivity |
| 2 | Prepare concentrated buffers (see Table 4) |
| 3 | Prepare diluted buffers based on concentrated buffers (see Table 4) to compare with original buffers and measure amount of NaOH/HCl to be used for pH-adjustment |

TABLE 2-continued

Test setup for preparing of concentrated buffers.

| Activity | Description |
|---|---|
| 4 | Adjust concentrated buffers (according to required acid/base used at "3" to reach target), recalculate composition of concentrated buffers, update buffer sheets of relevant concentrated buffers and repeat experiment 2 and 3. |
| 5 | Test of in-line dilution of final concentrated buffers e.g. by use of Äkta Avant to compare with original buffers. |

TABLE 3

Test conditions of experiments for concentrated buffers

| Experiment | Buffer | Purpose | Composition | LEP no. # |
|---|---|---|---|---|
| 1 | B | Column | 0.1M Sodium Hydroxide | LEP.2733 |
| 2 | B10 | CIP | 1M Sodium Hydroxide | LEP.2733 |
| 3 | B-Dil | | 0.1M Sodium Hydroxide by: 10% Buffer B10, 90% HPW | LEP.2733 |
| 4 | E | Equilibration | 20 mM sodium phosphate, 150 mM NaCl, pH 7.0 ± 0.2 | LEP.2733 |
| 5 | E10 | and wash | 200 mM sodium phosphate, 1.5M NaCl, pH "7.0" ± 0.2 | LEP.2733 |
| 6 | E-Dil | | 20 mM sodium phosphate, 150 mM NaCl, pH 7.0 ± 0.2 by: 10% Buffer E10, 90% HPW | LEP.2733 |
| 7 | F | Elution | 20 mM citrate, 100 mM NaCl pH 3.4 ± 0.2 | LEP.2733 |
| 8 | F10 | | 200 mM citrate, 1.0M NaCl, pH "3.4" ± 0.2 | LEP.2733 |
| 9 | F-Dil | | 20 mM citrate, 100 mM NaCl pH 3.4 ± 0.2 by: 10% Buffer F10, 90% HPW | LEP.2733 |

Test of Concentrated Buffers

Three concentrated buffers, which are central for the chromatography, were prepared at 10 times the normal buffer concentration. These were buffers B10, E10 and F10 (see Table 4 above) used for column CIP, equilibration and elution respectively. The specific procedure for development of concentrated buffers includes:

1. Prepare original buffer in triplicate
   Measure in triplicate pH, conductivity and if relevant other relevant parameter of buffer
2. Prepare concentrated buffer
   Measure pH, conductivity and if relevant other relevant parameter of concentrated buffer
3. Dilute concentrated buffer to the original concentration
   Measure pH, conductivity and if relevant other relevant parameter of diluted buffer
4. Compare the original and diluted buffer and determine the off-set of pH
5. Determine the off-set of pH in the concentrated buffer
6. Prepare concentrated buffer after adjustment for the off-set
7. Repeat point 3. If pH is within acceptance criteria, the concentrated buffer is approved. Otherwise repeat step 4 to 6.

The pH-value of the original buffer is the set point for buffer, which is prepared based on a concentrated buffer. The success criterion for preparation of a concentrated buffer is that the pH-value of this buffer after dilution has the same pH-value as the original buffer ±0.2. The conductivity is used as control of a correct composition of buffer components, which is likely when the conductivity is within range compare to the original buffer.

The pH of the concentrated buffer is corrected if needed by measuring the off-set in a diluted buffer and the amount of acid or base used for adjusting pH to set point of the diluted buffer. The same amount of acid or based used to adjust 1 L diluted buffer was added to 100 mL concentrated buffer. Thereby the correct pH of the concentrated buffer was determined and a buffer composition resulting in this pH-value was established by use of a standard buffer tool.

Testing.

Concentrated buffers, at 10 times the normal buffer concentration were prepared for the buffers shown in Table 7.

TABLE 7

Buffers used as models for preparation of concentrated buffers.

| No. | Name |
| --- | --- |
| Buffer B | 0.1M Sodium Hydroxide |
| Buffer E | 20 mM sodium phosphate, 150 mM NaCl, pH 7.0 ± 0.2 |
| Buffer F | 20 mM citrate, 100 mM NaCl, pH 3.4 ± 0.2 |

Using specific procedure for development of concentrated buffers discussed above the off-set pH of diluted buffers, based on a 10 times concentrated buffer, was determined. Data for preparation of a 10 times concentrated buffer E (buffer E10) is shown below.

1. 20 mM sodium phosphate, 150 mM NaCl, pH 7.0 is prepared three times pH is measured to 7.02; 7.03 and 7.08 respectively having an average at 7.04
   Conductivity is measured to 17.41; 17.56 and 17.58 respectively having an average at 17.52 mS/cm
2. 200 mM sodium phosphate, 1.5 M NaCl, pH 7.0
   Measure pH, conductivity and if relevant other relevant parameter of concentrated buffer
3. Dilute concentrated buffer to the original concentration
   Measure pH, conductivity and if relevant other relevant parameter of diluted buffer
4. Compare the original and diluted buffer and determine the off-set of pH
5. Determine the off-set of pH in the concentrated buffer
6. Prepare concentrated buffer after adjustment for the off-set
7. Repeat point 3. If pH is within acceptance criteria, the concentrated buffer is approved. Otherwise repeat step 4 to 6.

The pH-value of buffer E10 is 6.14 resulting in a pH-value after dilution at 6.83 having a set point at 7.00. This difference in pH between the diluted buffer and the original buffer is on the border of the acceptance criteria, why an adjustment of the concentrated buffer was initiated. Using the specific procedure for development of concentrated buffers discussed above, buffer E10 was corrected resulting in data shown below.

The preparation and adjustment of buffer B10 and F10 was carried out after the same principles (results not shown).

The pH-value of buffer F10 was 2.84 resulting in a pH-value after dilution at 3.25 having a set point at 3.40. This difference in pH between the diluted buffer and the original buffer was on the border of the acceptance criteria, why an adjustment of the concentrated buffer was initiated. Using the specific procedure for development of concentrated buffers discussed above, buffer F10 was corrected resulting in a pH-value after dilution at 3.49, which is very close to the set point at 3.40.

The conductivity of buffer B10 was 187.2 mS/cm resulting in conductivity after dilution at 22.9 mS/cm. No set point was established but the conductivity of the original buffer was 22.13 mS/cm and accordingly the difference of conductivity between the diluted buffer and the original buffer was very small and no adjustment was carried out.

CONCLUSION

A model for preparing 10 times concentrated buffers to enable a 10 times dilution reaching the pH and conductivity of the original buffer was established. The procedure for pH-adjustment of concentrated buffers, resulting in diluted buffers within the acceptance criteria and very close to the set point of the original buffers, was obtained.

No problem with solubility or precipitation was observed during preparation and storage of concentrate buffers at room temperature.

What is claimed is:

1. A method for producing a biopolymer using a chromatography system (20), wherein the chromatography system comprises:
   an eluting system (10) and a capturing system (11), wherein the capturing system (11) comprises a feed container (1) for holding a medium comprising the biopolymer and waste products, wherein the feed container (1) has an outlet (16),
   a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15),
   wherein the outlet (16) of the feed container (1) is in fluid connection with the inlet (12) of the first chromatography unit (2) and in fluid connection with the inlet (14) of the second chromatography unit (3), wherein a first valve means (31) is located between the outlet (16) and the inlet (12), and a second valve means (32) is located between the outlet (16) and the inlet (14),
   wherein the outlet (13) of the first chromatography unit (2) is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) is in fluid connection with the inlet (12) of the first chromatography unit (2), and a fourth valve means (34) is located between the outlet (15) of the second chromatography unit (3) and the inlet (12) of the first chromatography unit (2);
wherein the eluting system (10) comprises a wash buffer container (4), having an outlet (21), an elution buffer container (5), having an outlet (22), optionally a cleaning buffer container (6), having an outlet (23), optionally an equilibration buffer container (7), having an outlet (24), a water supply (8), having an outlet (25), an inline buffer dilution system (9) having an inlet (26a) and an outlet (27), wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9), wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9),
optionally, wherein the outlet (23) of the cleaning buffer container (6) is in fluid connection with the inlet (26a) of the inline buffer dilution system (9) and wherein a seventh valve means (37) is located between the outlet (23) of the cleaning buffer container (6) and the inlet (26a) of the inline buffer dilution system (9),
optionally, wherein the outlet (24) of the equilibration buffer container (7) is in fluid connection with the inlet (26a) of the inline buffer dilution system (9) and wherein an eighth valve means (38) is located between the outlet (24) of the equilibration buffer container (7) and the inlet (26a) of the inline buffer dilution system (9),
wherein the outlet (25) of the water supply (8) is in fluid connection with the inlet (26a) of the inline buffer dilution system (9) or is in fluid connection with a separate inlet (26b) of the inline buffer dilution system (9) and wherein a ninth valve means (39) is located between the outlet (25) of the water supply (8) and the inlet (26a) or the separate inlet (26b) of the inline buffer dilution system (9); and
wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3),
the method comprising:
(a) leading a medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2) until a first pre-determined level of binding capacity is reached in the chromatography unit (2), wherein the fluid connection from the outlet (16) of the feed container (1) to the inlet (14) of the second chromatography unit (3) is closed by the second valve means (32) and wherein the fluid connection from the outlet (13) of the first chromatography unit (2) to the inlet (14) of the second chromatography unit (3) is closed by the third valve means (33),
(b) when the first pre-determined level of binding capacity is reached, leading the medium comprising the biopolymer and waste products through the fluid connection from the outlet (13) of the first chromatography unit (2) to the inlet (14) of the second chromatography unit (3) and through the second chromatography unit (3) for a specified setting for the biopolymer un-captured by the first chromatography unit (2) to be captured on the second chromatography unit (3), and medium and waste products continues through the outlet (15) of the chromatography unit (3), until a second pre-determined level of binding capacity is reached in the chromatography unit (2) and/or (3), wherein the fluid connection from the outlet (16) of the feed container (1) to the inlet (14) of the second chromatography unit (3) is closed by the second valve means (32),
(c) when the second pre-determined level of binding capacity is reached, leading the medium comprising the biopolymer and waste products through the fluid connection from the outlet (16) of the feed container (1) to the inlet (14) of the chromatography unit (3) wherein the biopolymer is captured on the chromatography unit (3), and medium and waste products continues through the outlet (15) of the chromatography unit (3), until a third pre-determined level of binding capacity is reached in the chromatography unit (2) and/or (3), wherein the fluid connection from the outlet (16) of the feed container (1) to the inlet (12) of the first chromatography unit (2) is closed by the first valve means (31), and wherein the fluid connection from the outlet (15) of the second chromatography unit (3) to the inlet (12) of the first chromatography unit (2) is closed by the fourth valve means (34),
wherein during or after step c)
(i) washing the first chromatography unit (2) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (12) of the first chromatography unit (2), through the first chromatography unit (2), and through the outlet (13) of the first chromatography unit (2), until a first pre-determined level of washing is reached, wherein the fluid connection from the outlet (27) of the inline buffer dilution system (9) to the inlet (14) of the second chromatography unit (3) is closed by the eleventh valve means (41), (ii) when the first pre-determined level of washing is reached, eluting the biopolymer from the chromatography unit (2) by leading:
(a1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(a2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the working solution ready elution buffer the outlet (27) of the inline buffer dilution system (9) to the inlet (12) of the first chromatography unit (2), through the first chromatography unit (2), and through the outlet (13) of the first chromatography unit (2), until a first pre-determined level of eluting is reached, and collecting the eluate, wherein the fluid connection from the outlet (27) of the inline buffer dilution system (9) to the inlet (14) of the second chromatography unit (3) is closed by the eleventh valve means (41), (d) when the third pre-determined level of binding capacity is reached, leading the medium through the fluid connection from the outlet (15) of the second chromatography unit (3) to the inlet (12) of the first chromatography unit (2) and through the first chromatography unit (2) for a specified setting for the biopolymer un-captured by the second chromatography unit (3) to be captured on the first chromatography unit (2), and medium and waste products continues through the outlet (13) of the chromatography unit (2) until a fourth pre-determined level of binding capacity is reached in the chromatography unit (2) and/or (3), wherein the fluid connection from the outlet (16) of the feed container (1) to the inlet (12) of the first chromatography unit (2) is closed by the first valve means (31), (e) when the fourth pre-determined level of binding capacity is reached, leading the medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2), until a fifth pre-determined level of binding capacity is reached in the chromatography unit (2) and/or (3), wherein the fluid connection from the outlet (16) of the feed container (1) to the inlet (14) of the second chromatography unit (3) is closed by the second valve means (32), wherein during or after step e)

(iii) washing the chromatography unit (3) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (14) of the second chromatography unit (3), through the second chromatography unit (3), and through the outlet (15) of the second chromatography unit (3), until a second pre-determined level of washing is reached, wherein the fluid connection from the outlet (27) of the inline buffer dilution system (9) to the inlet (12) of the first chromatography unit (2) is closed by the tenth valve means (40), (iv) when the second pre-determined level of washing is reached, eluting the biopolymer from the second chromatography unit (3) by leading:

(b1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(b2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the diluted elution buffer through the outlet (27) of the inline buffer dilution system (9) to the inlet (14) of the second chromatography unit (3), through the second chromatography unit (3), and through the outlet (15) of the second chromatography unit (3), until a second pre-determined level of eluting is reached, and collecting the eluate, wherein the fluid connection from the outlet (27) of the inline buffer dilution system (9) to the inlet (12) of the first chromatography unit (2) is closed by the tenth valve means (40), (f) optionally, repeating step (a) to (e), and (g) optionally, purifying the biopolymer from the collected eluate(s).

2. The method according to claim 1, wherein after step (ii);

(iib) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (13) of the first chromatography unit (2), through the first chromatography unit (2), and through the inlet (12) of the first chromatography unit (2), until a first pre-determined level of cleaning is reached, wherein the fluid connection from the outlet (27) of the inline buffer dilution system (9) to the inlet (12) of the first chromatography unit (2) is closed by the tenth valve means (40) and, wherein after step (iv);

(ivb) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (15) of the second chromatography unit (3), through the second chromatography unit (3), and through the inlet (14) of the second chromatography unit (3), until a second-determined level of cleaning is reached, wherein the fluid connection from the outlet (27) of the inline buffer dilution system (9) to the inlet (14) of the second chromatography unit (3) is closed by the eleventh valve means (41).

3. The method according to claim 1, wherein the biopolymer is a recombinant protein.

4. The method according to claim 1, wherein the biopolymer is a recombinant protein, wherein said recombinant protein is an antibody or a fragment thereof.

5. The method according to claim 1, wherein the medium in the feed container is kept at a temperature of 28-38° C.

6. The method according to claim 1, wherein the medium in the feed container is kept at a temperature of about 32° C.

7. The method according to claim 1, wherein the medium in the feed container is kept at a temperature of about 35° C.

8. The method according to claim 1, wherein the chromatography system further comprises a waste container (17) having an inlet (29) wherein the waste container (17) is in fluid connection with the outlet (13) of the first chromatography unit (2), wherein the third valve means (33) is located between the outlet (13) of the first chromatography unit (2) and the inlet (29) of the waste container (17).

9. The method according to claim 1, wherein the chromatography system further comprises a waste container (17) having an inlet (29) wherein the waste container (17) is in fluid connection with the outlet (15) of the second chromatography unit (3), wherein the fourth valve means (34) is located between the outlet (15) of the second chromatography unit (3) and the inlet (29) of the waste container (17).

10. The method according to claim 1, wherein the chromatography system further comprises rising an eluate container (18) having an inlet (28) wherein the eluate container (18) is in fluid connection with the outlet (13) of the first chromatography unit (2), wherein the third valve means (33) is located between the outlet (13) of the first chromatography unit (2) and the inlet (28) of the elution buffer container (18).

11. The method according to claim 1, wherein the chromatography system further comprises an eluate container (18) having an inlet (28) wherein the eluate container (18) is in fluid connection with the outlet (15) of the second chromatography unit (3), wherein the fourth valve means (34) is located between the outlet (15) of the second chromatography unit (3) and the inlet (28) of the eluate container (18).

12. The method according to claim 1, wherein the chromatography system further comprises a means for leading the medium comprising biopolymer and waste.

13. The method according to claim 12, wherein the means for leading the medium comprising biopolymer and waste is a pump.

14. The method according to claim 1, wherein the material having affinity for the biopolymer is a Protein A agarose based gel.

15. The method according to claim 1, wherein the chromatography system has no more than one first chromatography unit (2) and no more than one second chromatography unit (3).

16. A method for producing a biopolymer using a chromatography system (20) wherein the chromatography system comprises an eluting system (10) and a capturing system (11), wherein the capturing system (11) comprises a feed container (1) for holding a medium comprising the biopolymer and waste products, wherein the feed container (1) has an outlet (16), a first chromatography unit (2) and a second chromatography unit (3) both comprising material having affinity for the biopolymer, wherein the first chromatography unit (2) has an inlet (12) and an outlet (13) and the second chromatography unit (3) has an inlet (14) and an outlet (15), wherein the outlet (16) of the feed container (1) is in fluid connection with the inlet (12) of the first chromatography unit (2) and in fluid connection with the inlet (14) of the second chromatography unit (3), wherein a first valve means (31) is located between the outlet (16) and the inlet (12), and a second valve means (32) is located between the outlet (16) and the inlet (14), wherein the outlet (13) of the first chromatography unit (2) in the absence of a holding tank, is in fluid connection with the inlet (14) of the second chromatography unit (3), and a third valve means (33) is located between the outlet (13) of the first chromatography unit (2) and the inlet (14) of the second chromatography unit (3), and the outlet (15) of the second chromatography unit (3) in the absence of a holding tank, is in fluid connection with the inlet (12) of the first chromatography unit (2), and a fourth valve means (34) is located between the outlet (15) of the second chromatography unit (3) and the inlet (12) of the first chromatography unit (2), wherein biopolymer that is present in a flow-through from the first chromatography unit (2) in the absence of a holding tank, is captured on the second chromatography unit (3), and biopolymer that is present in a flow-through from the second chromatography unit (3) in the absence of a holding tank, is captured on the first chromatography unit (2);

wherein the eluting system (10) comprises, a wash buffer container (4), having an outlet (21), an elution buffer container (5), having an outlet (22), optionally a cleaning buffer container (6), having an outlet (23)

optionally an equilibration buffer container (7), having an outlet (24), a water supply (8), having an outlet (25), an inline buffer dilution system (9) having an inlet (26a) and an outlet (27), wherein the outlet (21) of the wash buffer container (4) is in fluid connection with the inlet (26a) of the inline buffer dilution system (9) and wherein a fifth valve means (35) is located between the outlet (21) of the wash buffer container (4) and the inlet (26a) of the inline buffer dilution system (9), wherein the outlet (22) of the elution buffer container (5) is in fluid connection with the inlet (26a) of the inline buffer dilution system (9) and wherein a sixth valve means (36) is located between the outlet (22) of the elution buffer container (5) and the inlet (26a) of the inline buffer dilution system (9), optionally, wherein the outlet (23) of the cleaning buffer container (6) is in fluid connection with the inlet (26*a*) of the inline buffer dilution system (9) and wherein a seventh valve means (37) is located between the outlet (23) of the cleaning buffer container (6) and the inlet (26*a*) of the inline buffer dilution system (9), optionally, wherein the outlet (24) of the equilibration buffer container (7) is in fluid connection with the inlet (26*a*) of the inline buffer dilution system (9) and wherein an eighth valve means (38) is located between the outlet (24) of the equilibration buffer container (7) and the inlet (26*a*) of the inline buffer dilution system (9), wherein the outlet (25) of the water supply (8) is in fluid connection with the inlet (26*a*) of the inline buffer dilution system (9) or is in fluid connection with a separate inlet (26*b*) of the inline buffer dilution system (9) and wherein a ninth valve means (39) is located between the outlet (25) of the water supply (8) and the inlet (26*a*) or the separate inlet (26*b*) of the inline buffer dilution system (9); and wherein the outlet (27) of the inline buffer dilution system (9) is in fluid connection with the inlet (12) of the first chromatography unit (2) and in fluid connection with the inlet (14) of the second chromatography unit (3), wherein a tenth valve means (40) is located between the outlet (27) of the inline buffer dilution system (9) and the inlet (12) of the first chromatography unit (2), and an eleventh valve means (41) is located between the outlet (27) of the inline buffer dilution system (9) and inlet (14) of the second chromatography unit (3), the method comprising:

(a) leading a medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2) until a first pre-determined level of binding capacity is reached in the chromatography unit (2), wherein the fluid connection from the outlet (16) of the feed container (1) to the inlet (14) of the second chromatography unit (3) is closed by the second valve means (32) and wherein the fluid connection from the outlet (13) of the first chromatography unit (2) to the inlet (14) of the second chromatography unit (3) is closed by the third valve means (33), (b) when the first pre-determined level of binding capacity is reached, leading the medium comprising the biopolymer and waste products through the fluid connection from the outlet (13) of the first chromatography unit (2) to the inlet (14) of the second chromatography unit (3) and through the second chromatography unit (3) for a specified setting for the biopolymer un-captured by the first chromatography unit (2) to be captured on the second chromatography unit (3), and medium and waste products continues through the outlet (15) of the chromatography unit (3), until a second pre-determined level of binding capacity is reached in the chromatography unit (2) and/or (3), wherein the fluid connection from the outlet (16) of the feed container (1) to the inlet (14) of the second chromatography unit (3) is closed by the second valve means (32), (c) when the second pre-determined level of binding capacity is reached, leading the medium comprising the biopolymer and waste products through the fluid connection from the outlet (16) of the feed container (1) to the inlet (14) of the chromatography unit (3) wherein the biopolymer is captured on the chromatography unit (3), and medium and waste products continues through the outlet (15) of the chromatography unit (3), until a third pre-determined level of binding capacity is reached in the chromatography unit (2) and/or (3), wherein the fluid connection from the outlet (16) of the feed container (1) to the inlet (12) of the first chromatography unit (2) is closed by the first valve means (31), and wherein the fluid connection from the outlet (15) of the second chromatography unit (3) to the inlet (12) of the first chromatography unit (2) is closed by the fourth valve means (34), wherein during or after step c)

(i) washing the first chromatography unit (2) with a specified concentration of water and buffer by leading concentrated wash buffer through the fluid connection from the outlet (21) of the wash buffer container (4) to the inlet (26*a*) of the inline buffer dilution system (9) and by leading the water from the supply (8) through the fluid connection from the outlet (25) of the water from the supply (8) to the inlet (26*a*) or the inlet (26*b*) of the inline buffer dilution system (9) wherein the fluid connection from the outlet (22) of the elution buffer container (5) to the inlet (26*a*) of the inline buffer dilution system (9) is closed by the sixth valve means (36), and leading the diluted wash buffer through the outlet (27) of the inline buffer dilution system (9) to the inlet (12) of the first chromatography unit (2), through the first chromatography unit (2), and through the outlet (13) of the first chromatography unit (2), until a first pre-determined level of washing is reached, wherein the fluid connection from the outlet (27) of the inline buffer dilution system (9) to the inlet (14) of the second chromatography unit (3) is closed by the eleventh valve means (41), (ii) when the first pre-determined level of washing is reached, eluting the biopolymer from the chromatography unit (2) by leading:

(a1) concentrated elution buffer through the fluid connection from the outlet (22) of the elution buffer container (5) to the inlet (26*a*) of the inline buffer dilution system (9) and by leading the water from the supply (8) through the fluid connection from the outlet (25) of the water from the supply (8) to the inlet (26*a*) or the inlet (26*b*) of the inline buffer dilution system (9) or alternatively by leading:

(a2) a working solution ready elution buffer through the fluid connection from the outlet (22) of the elution buffer container (5) to the inlet (26*a*) of the inline buffer dilution system (9), wherein the fluid connection from the outlet (21) of the wash buffer container (4) to the inlet (26*a*) of the inline buffer dilution system (9) is closed by the fifth valve means (35) and, wherein when the working solution ready elution buffer is used the fluid connection from the outlet (25) of the water supply (8) to the inlet (26*a*) or the inlet (26*b*) of the inline buffer dilution system (9) is closed by the ninth valve means (39) and leading the working solution ready elution buffer the outlet (27) of the inline buffer dilution system (9) to the inlet (12) of the first chromatography unit (2), through the first chromatography unit (2), and through the outlet (13) of the first chromatography unit (2), until a first pre-determined level of eluting is reached, and collecting the eluate, wherein the fluid connection from the outlet (27) of the inline buffer dilution system (9) to the inlet (14) of the second chromatography unit (3) is closed by the eleventh valve means (41), (d) when the third pre-determined level of binding capacity is reached, leading the medium through the fluid connection from the outlet (15) of the second chromatography unit (3) to the inlet (12) of the first chromatography unit (2) and through the first chromatography unit (2) for a specified setting for the biopolymer un-captured by the second chromatography unit (3) to be captured on the first chromatography unit (2), and medium and waste products continues through the outlet (13) of the chromatography unit (2) until a fourth pre-determined level of binding capacity is reached in the chromatography unit (2) and/or (3), wherein the fluid connection from the outlet (16) of the feed container (1) to the inlet (12) of the first chromatography unit (2) is closed by the first valve means (31), (e) when the fourth pre-determined level of binding capacity is reached, leading the medium comprising the biopolymer and waste products through the fluid connection from the outlet (16) of the feed container (1) to the inlet (12) of the chromatography unit (2) wherein the biopolymer is captured on the chromatography unit (2), and medium and waste products continues through the outlet (13) of the chromatography unit (2), until a fifth pre-determined level of binding capacity is reached in the chromatography unit (2) and/or (3), wherein the fluid connection from the outlet (16) of the feed container (1) to the inlet (14) of the second chromatography unit (3) is closed by the second valve means (32), wherein during or after step e)

(iii) washing the chromatography unit (3) with a specified concentration of water and buffer by leading concentrated wash buffer through the fluid connection from the outlet (21) of the wash buffer container (4) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (22) of the elution buffer container (5) to the inlet (26a) of the inline buffer dilution system (9) is closed by the sixth valve means (36), and leading the diluted wash buffer through the outlet (27) of the inline buffer dilution system (9) to the inlet (14) of the second chromatography unit (3), through the second chromatography unit (3), and through the outlet (15) of the second chromatography unit (3), until a second pre-determined level of washing is reached, wherein the fluid connection from the outlet (27) of the inline buffer dilution system (9) to the inlet (12) of the first chromatography unit (2) is closed by the tenth valve means (40), (iv) when the second pre-determined level of washing is reached, eluting the biopolymer from the second chromatography unit (3) by leading:

(b1) concentrated elution buffer through the fluid connection from the outlet (22) of the elution buffer container (5) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) or alternatively by leading:

(b2) a working solution ready elution buffer through the fluid connection from the outlet (22) of the elution buffer container (5) to the inlet (26a) of the inline buffer dilution system (9), wherein the fluid connection from the outlet (21) of the wash buffer container (4) to the inlet (26a) of the inline buffer dilution system (9) is closed by the fifth valve means (35) and, wherein when the working solution ready elution buffer is used the fluid connection from the outlet (25) of the water supply (8) to the inlet (26a) or the inlet (26b) of the inline buffer dilution system (9) is closed by the ninth valve means (39) and leading the diluted elution buffer through the outlet (27) of the inline buffer dilution system (9) to the inlet (14) of the second chromatography unit (3), through the second chromatography unit (3), and through the outlet (15) of the second chromatography unit (3), until a second pre-determined level of eluting is reached, and collecting the eluate, wherein the fluid connection from the outlet (27) of the inline buffer dilution system (9) to the inlet (12) of the first chromatography unit (2) is closed by the tenth valve means (40), (f) optionally, repeating step (a) to (e), and (g) optionally, purifying the biopolymer from the collected eluate(s).

17. The method according to claim 16, wherein after step (ii);

(iia) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of cleaning is reached, wherein the fluid connection from the outlet (27) of the inline buffer dilution system (9) to the inlet (14) of the second chromatography unit (3) is closed by the eleventh valve means (41) and, wherein after step (iv);

(iva) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (14) of the second chromatography unit (2), through the second chromatography unit (3), and through the outlet (15) of the second chromatography unit (3), until a second-determined level of cleaning is reached, wherein the fluid connection from the outlet (27) of the inline buffer dilution system (9) to the inlet (12) of the first chromatography unit (2) is closed by the tenth valve means (40).

18. The method according to claim 17, wherein after step (iia);

(iic) equilibrating the first chromatography unit (2) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the inlet (12) of the first chromatography unit (2), until a first pre-determined level of equilibration is reached, wherein the fluid connection from the outlet (27) of the inline buffer dilution system (9) to the inlet (14) of the second chromatography unit (3) is closed by the eleventh valve means (41), and wherein after step (iva) or (ivb);

(ivc) equilibrating the second chromatography unit (3) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of equilibration is reached, wherein the fluid connection from the outlet (27) of the inline buffer dilution system (9) to the inlet (12) of the first chromatography unit (2) is closed by the valve means (40).

19. The method according to claim 11, wherein after step (iib);

(iic) equilibrating the first chromatography unit (2) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the inlet (12) of the first chromatography unit (2), until a first pre-determined level of equilibration is reached, wherein the fluid connection from the outlet (27) of the inline buffer dilution system (9) to the inlet (14) of the second chromatography unit (3) is closed by the eleventh valve means (41), and wherein after step (iva) or (ivb);

(ivc) equilibrating the second chromatography unit (3) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of equilibration is reached, wherein the fluid connection from the outlet (27) of the inline buffer dilution system (9) to the inlet (12) of the first chromatography unit (2) is closed by the valve means (40).

20. The method according to claim 19, wherein the medium in the feed container is kept at a temperature of 28-38° C.

21. The method according to claim 9, wherein after step (ii);

(iia) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of cleaning is reached, wherein the fluid connection from the outlet (27) of the inline buffer dilution system (9) to the inlet (14) of the second chromatography unit (3) is closed by the eleventh valve means (41) and, wherein after step (iv);

(iva) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the inlet (14) of the second chromatography unit (2), through the second chromatography unit (3), and through the outlet (15) of the second chromatography unit (3), until a second-determined level of cleaning is reached, wherein the fluid connection from the outlet (27) of the inline buffer dilution system (9) to the inlet (12) of the first chromatography unit (2) is closed by the tenth valve means (40).

22. The method according to claim 2, wherein after step (iia);

(iic) equilibrating the first chromatography unit (2) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the inlet (12) of the first chromatography unit (2), until a first pre-determined level of equilibration is reached, wherein the fluid connection from the outlet (27) of the inline buffer dilution system (9) to the inlet (14) of the second chromatography unit (3) is closed by the eleventh valve means (41), and wherein after step (iva) or (ivb);

(ivc) equilibrating the second chromatography unit (3) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of equilibration is reached, wherein the fluid connection from the outlet (27) of the inline buffer dilution system (9) to the inlet (12) of the first chromatography unit (2) is closed by the valve means (40).

23. The method according to claim 9, wherein after step (ii);

(iib) cleaning the first chromatography unit (2) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (13) of the first chromatography unit (2), through the first chromatography unit (2), and through the inlet (12) of the first chromatography unit (2), until a first pre-determined level of cleaning is reached, wherein the fluid connection from the outlet (27) of the inline buffer dilution system (9) to the inlet (12) of the first chromatography unit (2) is closed by the tenth valve means (40) and, wherein after step (iv);

(ivb) cleaning the second chromatography unit (3) with a specified concentration of water and buffer by leading concentrated cleaning buffer through the fluid connection from the outlet (23) of the cleaning buffer container (6) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elution buffer container (5) to the inlet (26a) of the inline buffer dilution system (9) is closed by the sixth valve means (36), and leading the diluted cleaning buffer through the outlet (27) of the inline buffer dilution system (9) to the outlet (15) of the second chromatography unit (3), through the second chromatography unit (3), and through the inlet (14) of the second chromatography unit (3), until a second-determined level of cleaning is reached, wherein the fluid connection from the outlet (27) of the inline buffer dilution system (9) to the inlet (14) of the second chromatography unit (3) is closed by the eleventh valve means (41).

24. The method according to claim 2, wherein after step (iib);
(iic) equilibrating the first chromatography unit (2) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the inlet (12) of the first chromatography unit (2), until a first pre-determined level of equilibration is reached, wherein the fluid connection from the outlet (27) of the inline buffer dilution system (9) to the inlet (14) of the second chromatography unit (3) is closed by the eleventh valve means (41),
and wherein after step (iva) or (ivb);
(ivc) equilibrating the second chromatography unit (3) with a specified concentration of water and buffer by leading concentrated equilibration buffer through the fluid connection from the outlet (24) of the equilibration buffer container (7) to the inlet (26a) of the inline buffer dilution system (9) and by leading the water from the supply (8) through the fluid connection from the outlet (25) of the water from the supply (8) to the inlet (26a) or the inlet (26b) of the inline buffer dilution system (9) wherein the fluid connection from the outlet (21) of the wash buffer container (4) to the inlet (26a) of the inline buffer dilution system (9) is closed by the fifth valve means (35), and wherein the fluid connection from the outlet (22) of the elute container (5) to the inlet (26a) of the inline buffer dilution system (9) is closed by the sixth valve means (36), and wherein the fluid connection from the outlet (23) of the cleaning buffer container (6) to the inlet (26a) of the inline buffer dilution system (9) is closed by the seventh valve means (37), and leading the diluted cleaning buffer through the outlet (27) of the inline buffer dilution system (9) to the inlet (12) of the first chromatography unit (2), through the first chromatography unit (2), and through the outlet (13) of the first chromatography unit (2), until a first pre-determined level of equilibration is reached, wherein the fluid connection from the outlet (27) of the inline buffer dilution system (9) to the inlet (12) of the first chromatography unit (2) is closed by the valve means (40).

25. The method according to claim 16, wherein the biopolymer is a recombinant protein.

26. The method according to claim 16, wherein the biopolymer is a recombinant protein, wherein said recombinant protein is an antibody or a fragment thereof.

* * * * *